(12) United States Patent
Simpson et al.

(10) Patent No.: US 8,998,937 B2
(45) Date of Patent: Apr. 7, 2015

(54) METHODS AND DEVICES FOR CUTTING TISSUE

(75) Inventors: John B. Simpson, Woodside, CA (US); Michael H. Rosenthal, Palo Alto, CA (US); Himanshu Patel, San Jose, CA (US); Gautama B. Venegas, Pleasanton, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/431,210

(22) Filed: Apr. 28, 2009

(65) Prior Publication Data

US 2009/0299394 A1 Dec. 3, 2009

Related U.S. Application Data

(63) Continuation of application No. 10/421,979, filed on Apr. 22, 2003, now Pat. No. 7,713,279, which is a continuation-in-part of application No. 10/288,581, filed on Nov. 4, 2002, now Pat. No. 7,887,556, which (Continued)

(51) Int. Cl.
*A61B 17/32* (2006.01)
*A61B 17/3207* (2006.01)
(Continued)

(52) U.S. Cl.
CPC . *A61B 17/320783* (2013.01); *A61B 17/320758* (2013.01); *A61B 2017/00685* (2013.01); *A61B 2017/2927* (2013.01); *A61B 2017/320032* (2013.01); *A61B 2017/320791* (2013.01); *A61B 2019/5206* (2013.01); *A61B 2019/5231* (2013.01); *A61B 2019/5278* (2013.01)

(58) Field of Classification Search
USPC .......... 606/159, 167, 170, 171, 180; 600/564
See application file for complete search history.

(56) References Cited

U.S. PATENT DOCUMENTS 1,481,078 A 1/1924 Albertson
2,178,790 A 11/1939 Henry
(Continued)

FOREIGN PATENT DOCUMENTS

CA 2000621 4/1990
DE 3732236 C1 12/1988
(Continued)

OTHER PUBLICATIONS

Brezinski et al., "Optical Coherence Tomography for Optical Biopsy," Circulation, 93:1206-1213 (1996).
(Continued)

*Primary Examiner* — Elizabeth Houston
*Assistant Examiner* — Son Dang
(74) *Attorney, Agent, or Firm* — Alana T. Bergman, Esq.

(57) ABSTRACT

A method of removing material from a blood flow lumen generally includes providing a device having a cutting element and an opening, advancing the device through the blood flow lumen to a site where material is to be removed, forcing the opening toward a wall of the site where material is to be removed, and moving the cutting element and the opening so that material in the blood flow lumen is cut by the cutting element and directed into the opening for removal as the cutting element and opening are moved through the blood flow lumen. In some embodiments, the device may be deflected or bent to force the opening toward a wall to remove material. The cutting element may be rotatable and may have an axis that is movable, that is not parallel to the longitudinal axis of the device, or both.

11 Claims, 26 Drawing Sheets

Related U.S. Application Data is a continuation-in-part of application No. 10/027,418, filed on Dec. 19, 2001, now Pat. No. 7,771,444.

(60) Provisional application No. 60/272,373, filed on Feb. 27, 2001, provisional application No. 60/257,704, filed on Dec. 20, 2000.

(51) Int. Cl.
*A61B 17/00* (2006.01)
*A61B 17/29* (2006.01)
*A61B 19/00* (2006.01)

(56) References Cited

U.S. PATENT DOCUMENTS

| | | |
|---|---|---|
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinksi et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford, III et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |

(56) References Cited

U.S. PATENT DOCUMENTS

| | | |
|---|---|---|
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A * | 5/1994 | Shturman ............... 606/159 |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |

(56) References Cited

U.S. PATENT DOCUMENTS

| | | |
|---|---|---|
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike et al. |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A * | 4/1999 | Hundertmark et al. ....... 606/171 |
| 5,902,245 A | 5/1999 | Yock |
| 5,906,627 A | 5/1999 | Spaulding |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,979,951 A | 11/1999 | Shimura |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,016,649 A | 1/2000 | Bock et al. |
| 6,019,778 A | 2/2000 | Wislon et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,039,693 A | 3/2000 | Seward et al. |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |

(56) References Cited

U.S. PATENT DOCUMENTS

| | | |
|---|---|---|
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antoniades et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 8,226,674 B2 | 7/2012 | Simpson et al. |
| 8,246,640 B2 | 8/2012 | Rosenthal et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson et al. |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |

(56) References Cited

U.S. PATENT DOCUMENTS

| | | |
|---|---|---|
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | WO 93/16642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | 01/15609 A1 | 3/2001 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | WO 2006/058223 A2 | 6/2006 |
| WO | WO 2006/066012 A2 | 6/2006 |

OTHER PUBLICATIONS

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

International Search Report and Written Opinion of PCT Application No. PCT/US04/12600, dated Jun. 13, 2008, 8 pages total.

International Search Report of PCT Application No. PCT/US04/12601, dated Jun. 30, 2005, 3 pages total.

U.S. Appl. No. 10/288,559, filed Nov. 4, 2002, Himanshu Patel et al. (59 pages).

U.S. Appl. No. 10/421,980, filed Apr. 22, 2003, John B. Simpson et al. (36 pages).

U.S. Appl. No. 10/288,582, filed Nov. 4, 2002, John B. Simpson et al. (48 pages).

Abstract of DE 44 44 166 A1 (1 page).

Mar. 27, 2009 Communication from the European Patent Office regarding corresponding EP Application No. 01 991 343.3 (7 pages).

Apr. 6, 2010 European Supplementary Search Report in European Application No. 04760156.2 (3 pages).

Abstract of JP2206452A (1 page).

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

Judkins Left Coronary Catheter, posted: Jan. 19, 2009, [online], [retrieved on Mar. 29, 2011], retrieved from the Cardiophile MD using Internet website <URL:http://cardiophile.org/2009/02/judkins-left-coronary-catheter.html> (3 pages).

Sep. 21, 2010 International Search Report and Written Opinion for corresponding PCT Application No. PCT/US2010/032558 (14 pages).

Jul. 19, 2011 Communication in European Application No. 04760155.4 (5 pages).

Translation of Aug. 15, 2007 mailed Japanese Patent Office Action, Application No. 1999-139033 (4 pages).

European Search Report regarding related application serial No. EP 07795342.0 dated Sep. 3, 2012, 6 pgs.

Extended European Search Report regarding related European Patent Application No. 13172807.3, dated Aug. 23, 2013, 6 pages.

European Search Report regarding related application serial No. EP 07809112.1 dated Apr. 23, 2013, 6 pgs.

Apr. 11, 2011 extended European Search Report for corresponding European Application No. 11151192.9 (6 pages).

(56) References Cited

OTHER PUBLICATIONS

Non-Final Office for U.S. Appl. No. 13/551,123, dated Apr. 17, 2014, 9 pages, Alexandria, Virginia, United States.
Non-Final Office for U.S. Appl. No. 13/674,581, dated May 9, 2014, 15 pages, Alexandria, Virginia, United States.
Notice of Allowance for U.S. Appl. No. 13/536,497, dated May 15, 2014, 10 pages, Alexandria, Virginia, United States.
Office Action for European Application No. 12 165 347.1, dated Jul. 14, 2014, 4 pages, Alexandria, Munich, Germany.
Final Office for U.S. Appl. No. 13/674,581, dated Dec. 26, 2014, 15 pages, Alexandria, Virginia, United States.

* cited by examiner

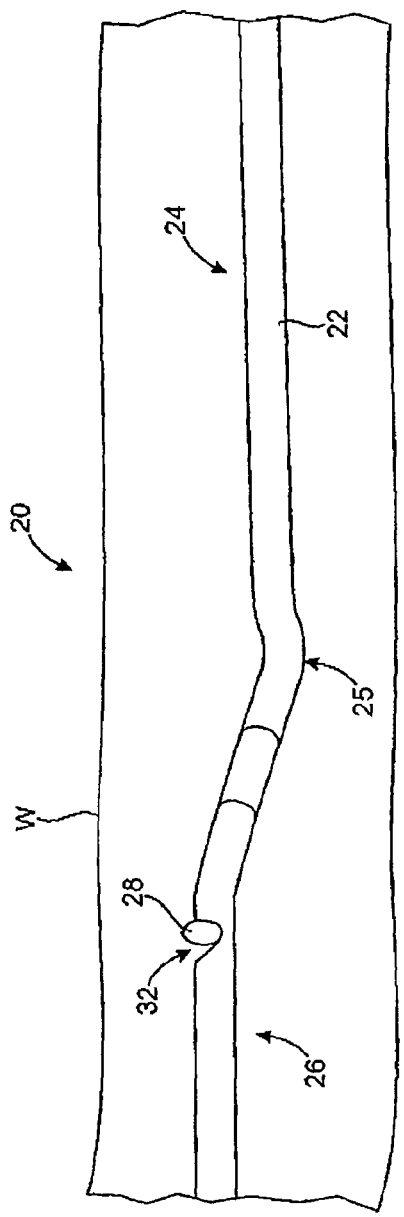

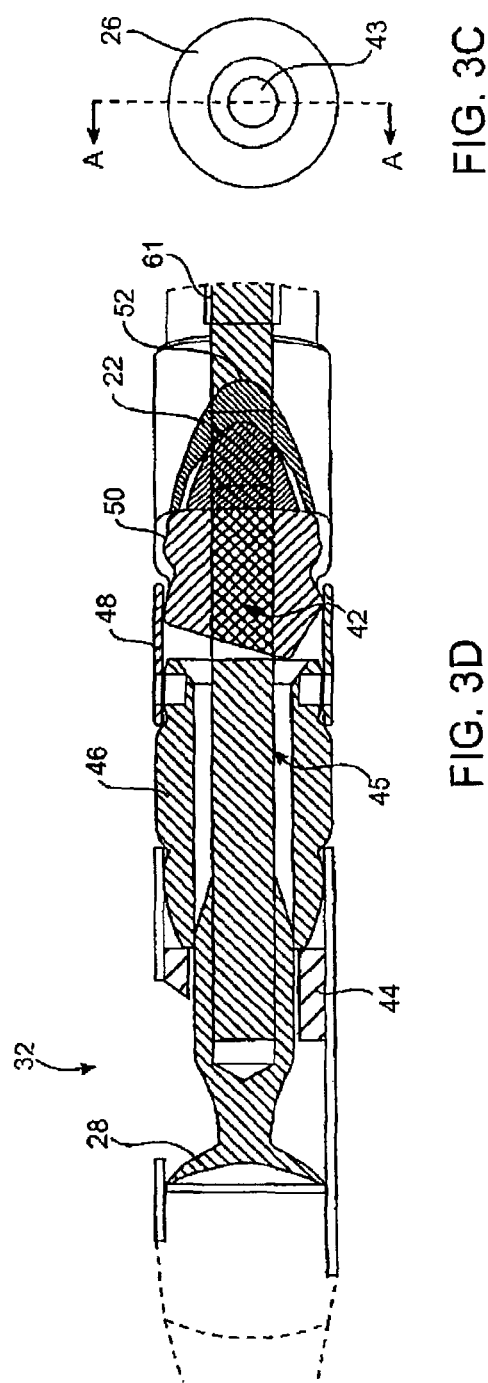

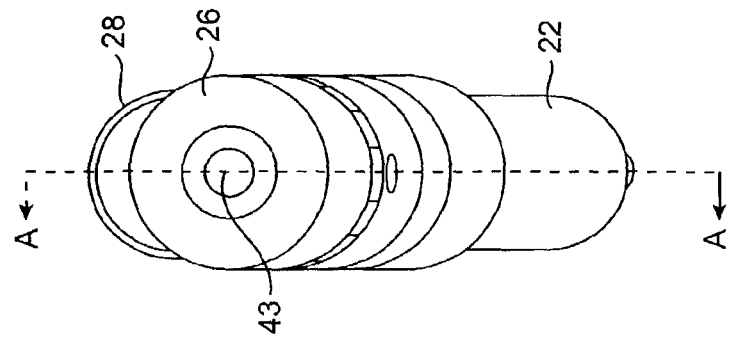
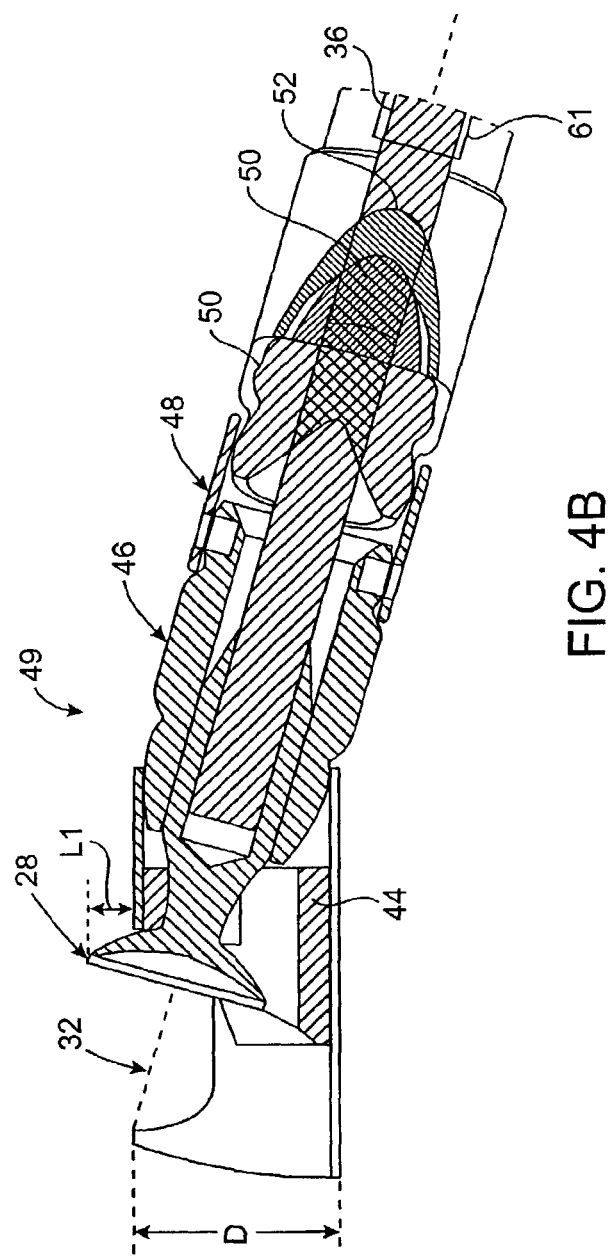

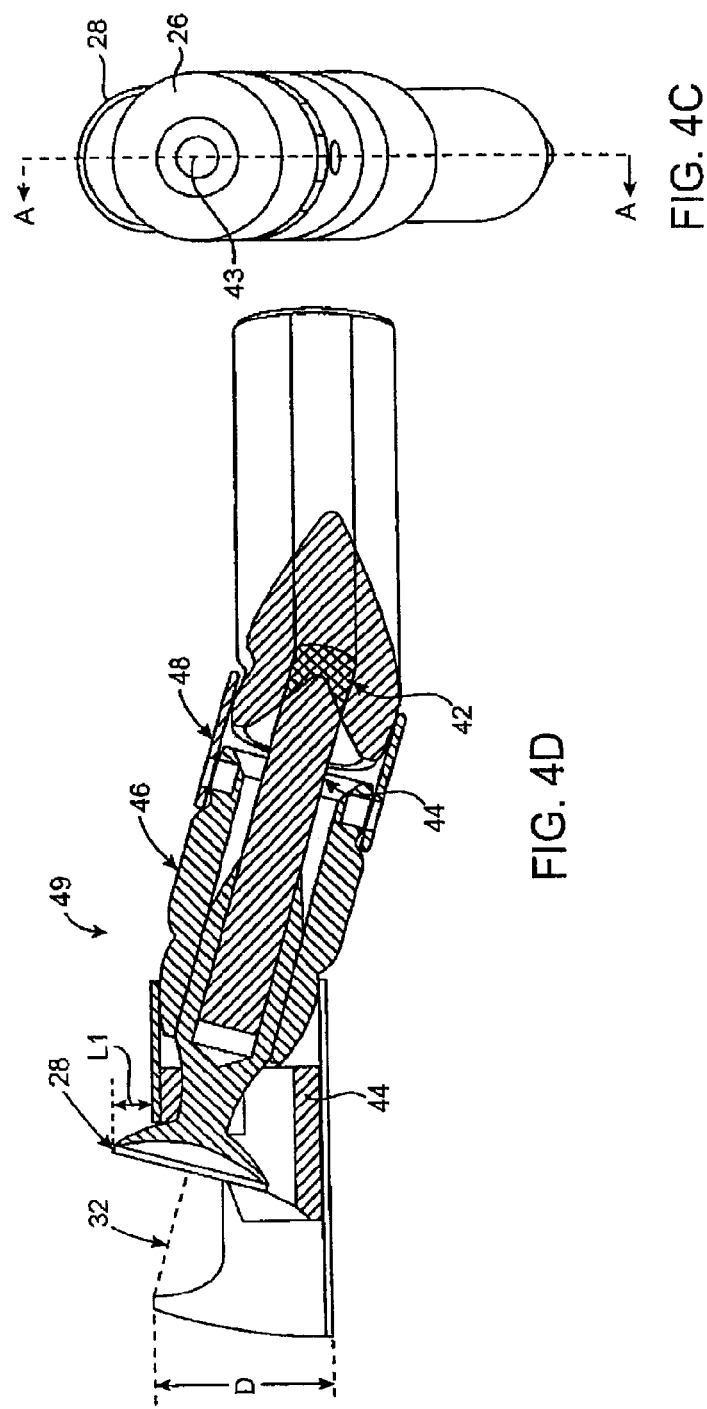

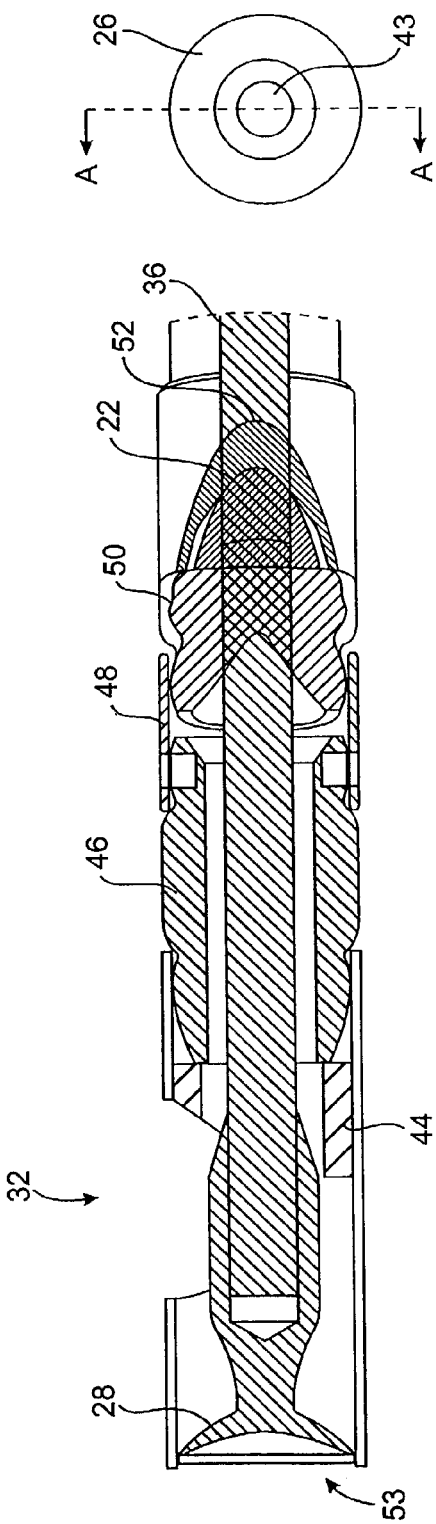

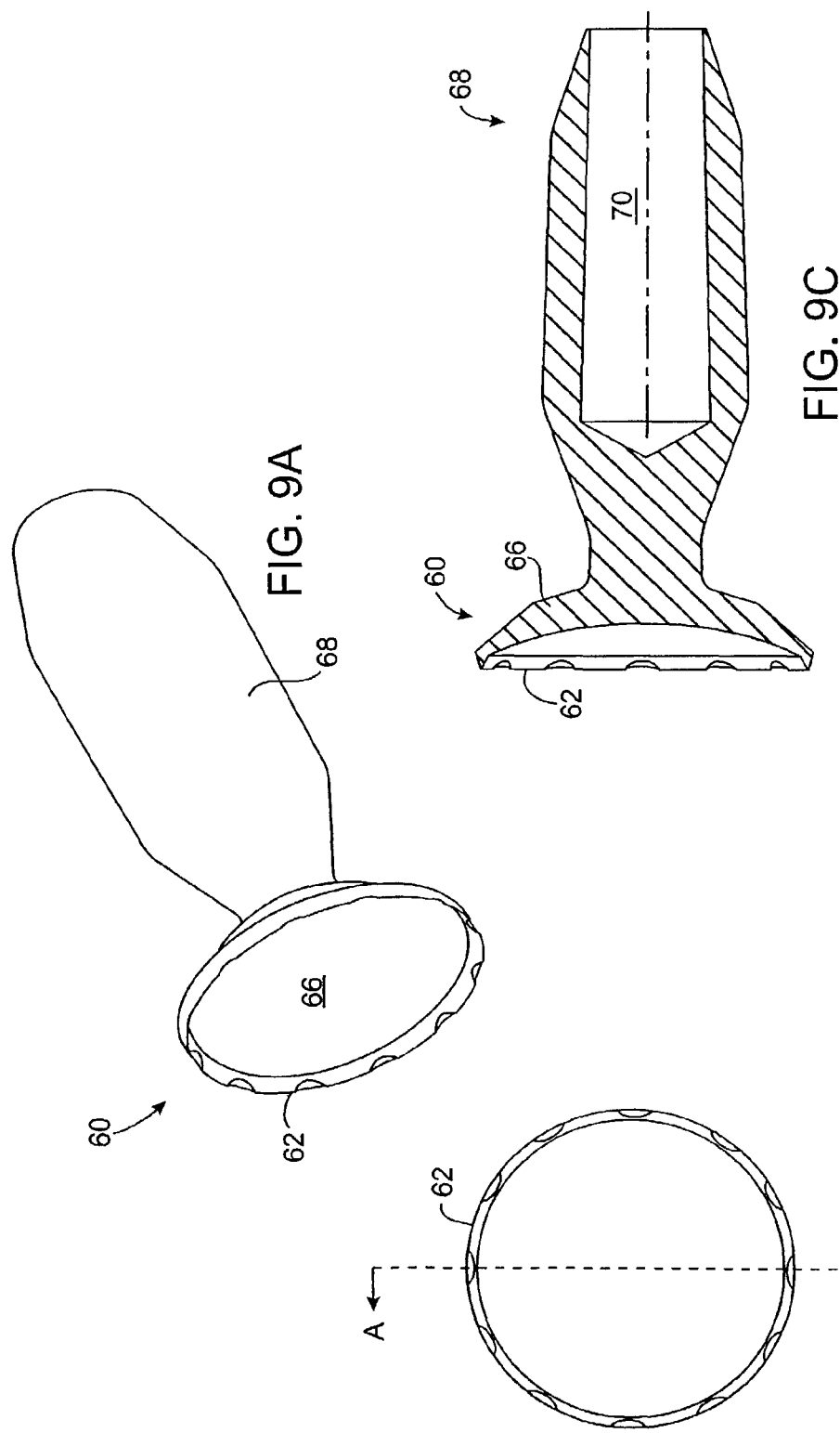

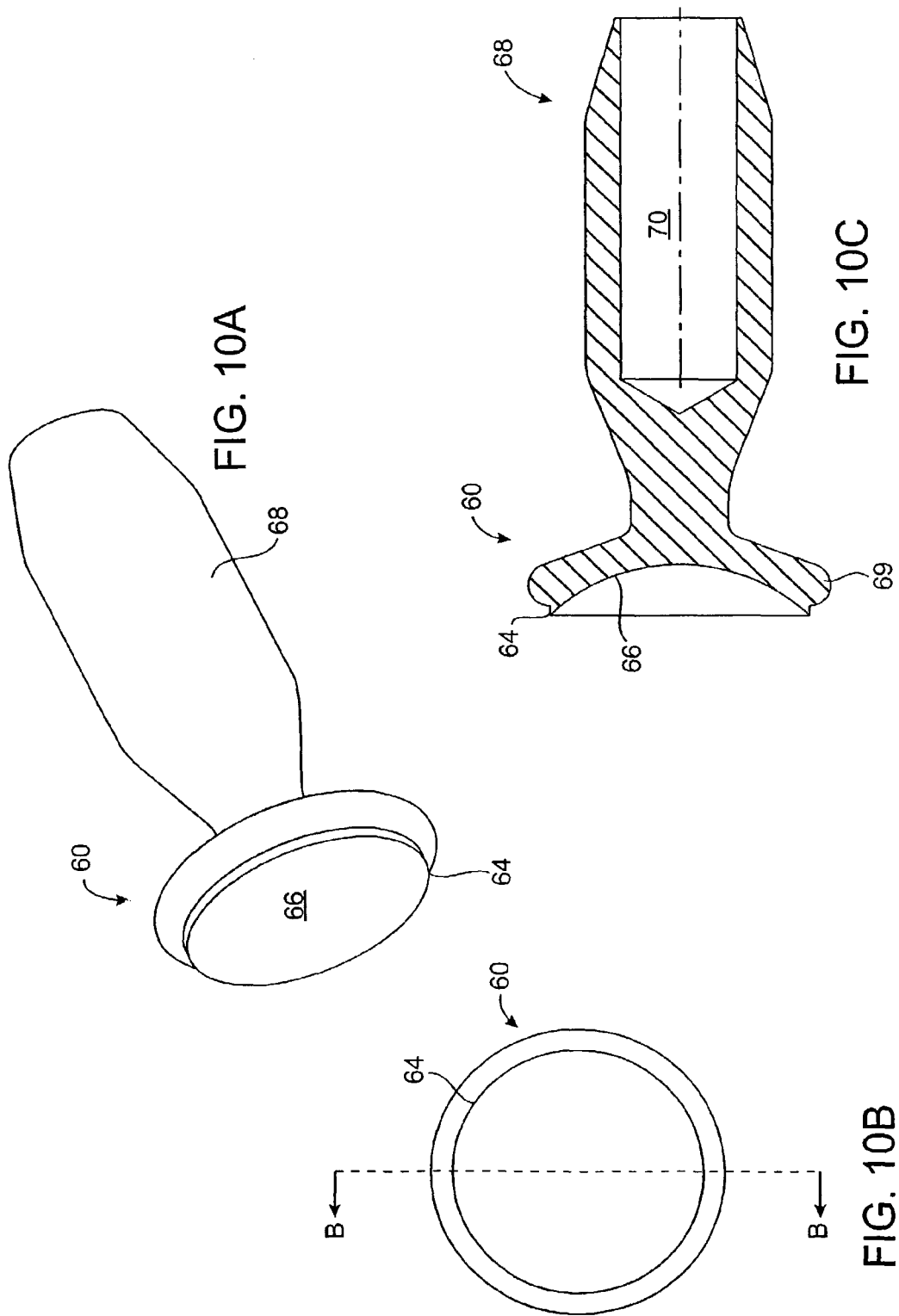

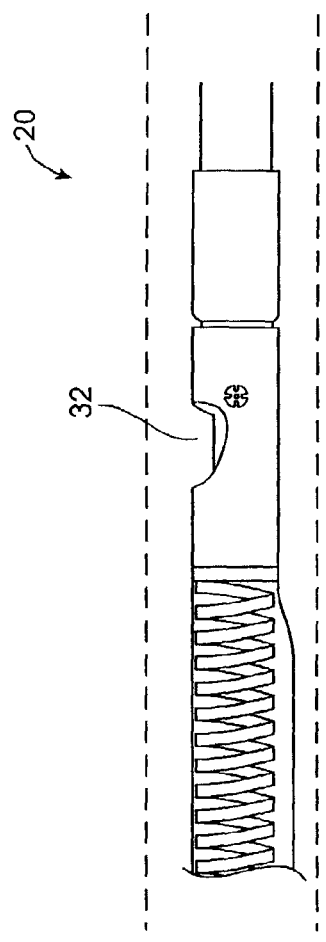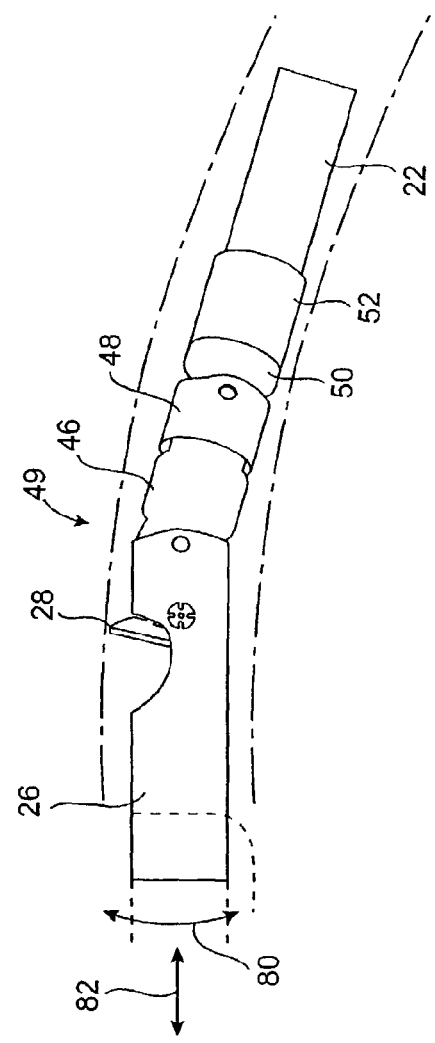

METHODS AND DEVICES FOR CUTTING TISSUE

CROSS-REFERENCES TO RELATED APPLICATIONS

The present application is a continuation of application Ser. No. 10/421,979, filed Apr. 22, 2003, now U.S. Pat. No. 7,713,279 B2, which is a continuation-in-part of application Ser. No. 10/288,581, filed Nov. 4, 2002, which is a continuation-in-part of U.S. patent application Ser. No. 10/027,418, filed Dec. 19, 2001, now U.S. Pat. No. 7,771,444 B2, which claims the benefit of Provisional Patent Application Ser. No. 60/257,704, filed Dec. 20, 2000, and Provisional Patent Application Ser. No. 60/272,273 filed Feb. 27, 2001, the contents of each of which are hereby incorporated by reference herein.

The present application is also related to U.S. patent application Ser. No. 09/377,884, filed Aug. 19, 1999, now U.S. Pat. No. 6,638,233 B2, entitled "Apparatus and Methods for Material Capture and Removal" and Ser. No. 09/377,894, filed Aug. 19, 1999, now U.S. Pat. No. 6,447,525 B2, entitled "Apparatus and Methods for Removing Material From a Body Lumen", the contents of each of which are hereby incorporated by reference herein.

BACKGROUND OF THE INVENTION

The present invention relates generally to systems and methods for debulking body lumens. More particularly, the present invention relates to atherectomy catheters for excising atheroma and other materials from blood vessels and from stents.

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

One conventional treatment for cardiovascular disease is the use of stents. Endoluminal stents are commonly used to treat obstructed or weakened body lumens, such as blood vessels and other vascular lumens. Once deployed in the blood vessel, the stent can remain in the body lumen where it will maintain the patency of the lumen and/or support the walls of the lumen which surround it. One factor impeding the success of stent technology in endoluminal treatments is the frequent occurrence of in-stent restenosis, characterized by proliferation and migration of smooth muscle cells within and/or adjacent to the implanted stent, causing reclosure or blockage of the body lumen.

Atherosclerosis and restenosis can be treated in a variety of ways, including drugs, bypass surgery, and a variety of catheter-based approaches which rely on intravascular debulking or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side, a blade which is rotated or translated by the aperture, and a balloon to urge the aperture against the material to be removed.

Although atherectomy catheters have proven very successful in treating many types of atherosclerosis and in-stent restenosis, improved atherectomy catheters and methods are continuously being pursued. For example, many currently available side-cutting atherectomy catheters have difficulty in capturing occluding material in the cutting aperture. To facilitate material capture, the cutting aperture is frequently elongated to increase the area into which the material can penetrate. Such elongation typically requires an equivalent lengthening of the cutter housing. Since most cutter housings are rigid, such lengthening makes it more difficult to introduce the distal end of the catheter through tortuous regions of the vasculature.

Another shortcoming of many currently available atherectomy catheters is that they typically require a balloon positioned opposite the cutting window to urge the cutting window into contact with occluding material. Such balloons, however, unduly increase the size of the distal portion of the catheter. Even with the balloon, the amount of material that can be removed by conventional atherectomy catheters is limited by the size of the cutting window. Other disadvantages of some catheters include cutting elements with less than ideal hardness, inadequate storage space within the catheter for containing removed material, sub-optimal guide wire lumens, and/or the like.

For these reasons, it would be advantageous to have atherectomy catheters, and methods for their use, which could access small, tortuous regions of the vasculature and remove atheromatous and other occluding materials from within blood vessels and stents in a controlled fashion. In particular, it would be desirable to have atherectomy catheters and methods which could facilitate capturing and invagination of atheromatous materials. Ideally, such catheters and methods would be adaptable for use in a variety of body lumens, including but not limited to coronary and other arteries. At least some of these objectives will be met by the present invention.

BRIEF SUMMARY OF THE INVENTION

The present invention provides catheters and methods for removing material from (or "debulking") a body lumen. Catheters of the present invention may be used in a variety of body lumens, including but not limited to intravascular lumens such as coronary arteries. Typically, debulking catheters are used to remove occlusive material, such as atherosclerotic plaque, from vascular lumens, but they may alternatively be used to remove other materials. Generally, debulking catheters include a proximal portion, a distal portion having an opening (or "window"), and a cutting element (or "tissue debulking assembly") which may be exposed through the opening to contact material in a body lumen. The catheter debulks a body lumen when it is moved while the cutting element is in contact with the material in the lumen.

In one aspect of the present invention, a method of removing material from a blood flow lumen comprises: providing a device having a cutting element and an opening; advancing the device through the blood flow lumen to a site where material is to be removed; forcing the opening toward a wall of the site where material is to be removed; and moving the cutting element and the opening after the forcing step so that material in the blood flow lumen is cut by the cutting element and directed into the opening for removal as the cutting element and opening are moved through the blood flow lumen. Optionally, the moving step may be carried out with the cutting element and the opening moving together in unison through the blood flow lumen.

In some embodiments, the forcing step is carried out by bending the device so that the opening is forced against the wall of the site. Also in some embodiments, the providing step is carried out with the cutting element being rotatable, with the moving step being carried out with the cutting element rotating when severing the material. When the cutting element is rotatable, the providing step may be carried out with the device having a longitudinal axis, and with the moving step being carried out with the cutting element rotating around an axis which is not parallel to the longitudinal axis of the device. In some embodiments, the providing step is carried out with the cutting element having an axis of rotation which is movable relative to a longitudinal axis of the device.

In some embodiments, the moving step is carried out with the cutting element cutting a continuous piece of material. Optionally, in such embodiments, the providing step may be carried out with the opening being on a side of the device; the forcing step may be carried out to force the side against the blood flow lumen; and the moving step may be carried out with the cutting element extending out of the opening, the cutting element directing the continuous piece of material into the opening. In some embodiments, the moving step is carried out by moving the cutting element and window in a distal direction, with the cut material being stored in the device at a location distal to the cutting element. Also in some embodiments, the providing step is carried out with the cutting element being movable relative to the opening.

In still other embodiments, the providing step is carried out with the cutting element being movable between a deployed position and a retracted position, the cutting element extending out of the opening when in the deployed position and being contained within the opening when in the retracted position. In such embodiments, the advancing step is typically carried out with the cutting element in the retracted position and the moving step is carried out with the cutting element being in the deployed position. For example, the providing step may be carried out with the cutting element extending beyond the opening a distance of about 0.025 mm to about 0.64 mm. Generally, the providing step may be carried out with the opening being positioned along a side of the device.

In still another aspect of the present invention, a device for cutting tissue is provided which has an elongate body with an opening therein. A rotatable cutting element is coupled to a torque transmitting element which extends through the body. A visualization element is movable from a stored position to a working position which is at a radially outward position on the body.

In yet another aspect of the present invention, a device for cutting tissue is provided which has a movable cover coupled to the body. The cover is movable from a stored position, in which the rotatable cutting element is covered by the cover, to a working position, in which at least part of the rotatable cutting element is exposed. The cover may be linearly movable relative to the body so that the cover essentially translates without deforming.

In another aspect of the invention, a method of removing material from a vascular location is provided. The body may be deformed before advancing the cutting element and opening through the vascular region to cut and remove a continuous piece of material as describe herein. The deformable portion of the body may take any suitable shape such as S-shaped or helical providing the step of forcing the opening toward a wall of the site where material is to be removed. The deformable portion may be relatively long, such as at least 1 cm or even at least 2 cm, to help stabilize the device.

In another aspect of the invention, a device for cutting tissue is provided which has two pivot points on opposite sides of the cutting element. The pivot points both help to move the cutting element into the cutting position and force the opening toward a wall. In particular the cutting or working position presents the cutting element at an orientation which may be advantageous when advancing the entire device through the vasculature as describe herein to cut and remove a continuous piece of material.

For a further understanding of the nature and advantages of the invention, reference should be made to the following description taken in conjunction with the accompanying drawings.

BRIEF DESCRIPTION OF THE DRAWINGS

FIG. 1A is a side view of a portion of a debulking catheter as in FIG. 1, where the body has a rigid distal portion with a bend, according to one embodiment of the present invention;

FIGS. 3C and 3D are views of the distal portion of a debulking catheter, where the distal portion has a locking shuttle mechanism;

FIG. 4A is an end view of the distal portion of the debulking catheter of FIG. 1 in which the cutter is in an open position outside of the cutting window;

FIG. 4B is a sectional view along Line A-A of FIG. 4A;

FIGS. 4C and 4D are views of the distal portion of a debulking catheter, where the distal portion has a locking shuttle mechanism;

FIG. 5A is an end view of the distal portion of the debulking catheter of FIG. 1 in which the cutter is in a packing position within a tip of the catheter;

FIG. 5B is a sectional view along Line A-A of FIG. 5A;

FIG. 9A is a perspective view of a cutter of the present invention;

FIG. 9B is an end view of the cutter of FIG. 9A;

FIG. 9C is a sectional view of the cutter along Line A-A of the cutter of FIGS. 9A and 9B;

FIG. 10A is a perspective view of a in-stent restenosis cutter of the present invention;

FIG. 10B is an end view of the cutter of FIG. 10A;

FIG. 10C is a sectional view of the cutter along Line B-B of the cutter of FIGS. 10A and 10B;

FIGS. 18 and 19 illustrate a method of the present invention;

DETAILED DESCRIPTION OF THE INVENTION

Figure 1:
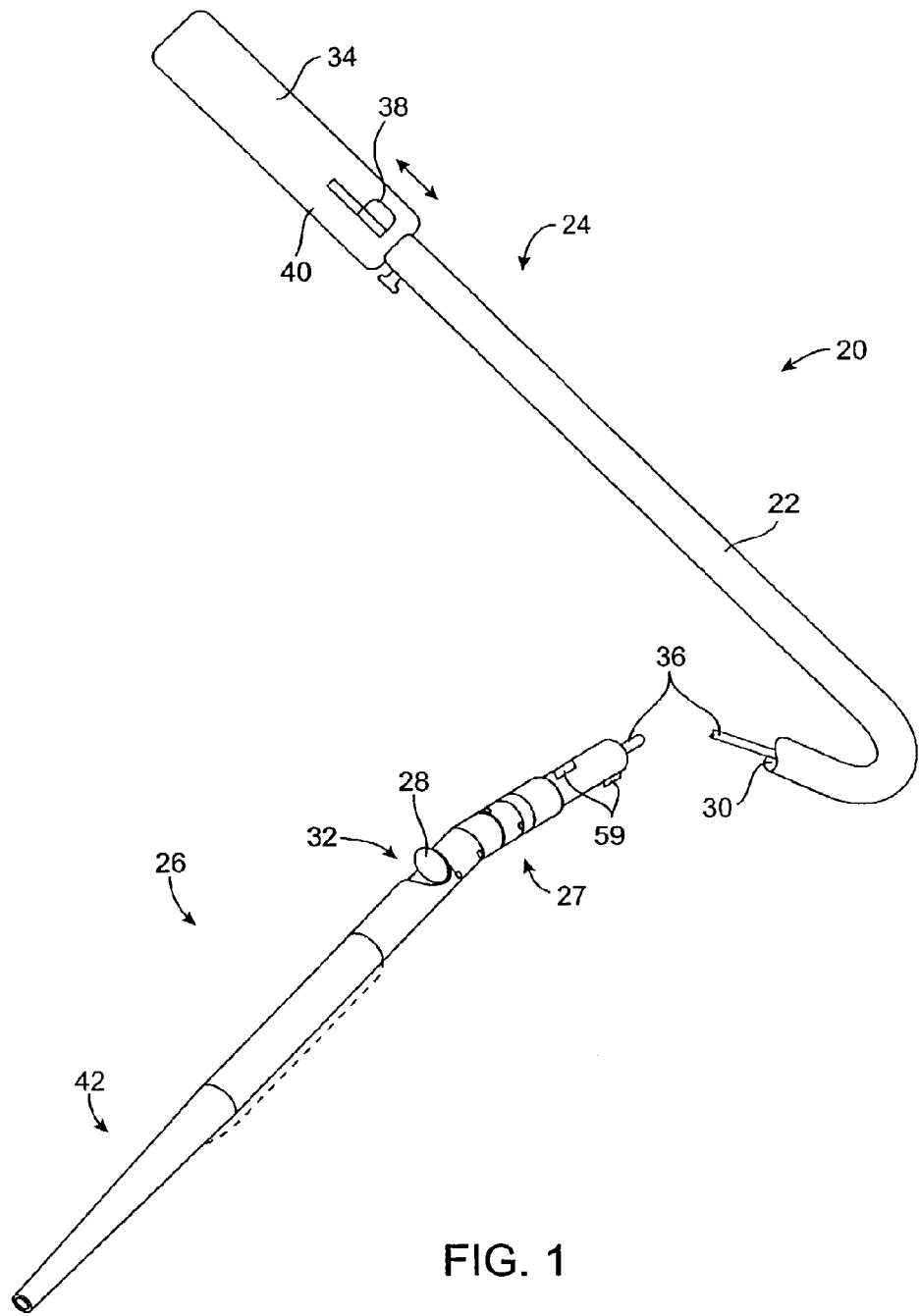
FIG. 1 is a perspective view of a debulking catheter of the present invention.

The catheters and methods of the present invention are designed to debulk atheroma and other occlusive material from diseased body lumens, and in particular coronary arteries, de novo lesions, and in-stent restenosis lesions. The catheters and methods, however, are also suitable for treating stenoses of body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Debulking of such material can thus be beneficial to maintain patency of the body lumen. While the remaining discussion is directed at debulking and passing through atheromatous or thrombotic occlusive material in a coronary artery, it will be appreciated that the systems and methods of the present invention can be used to remove and/or pass through a variety of occlusive, stenotic, or hyperplastic material in a variety of body lumens.

Apparatus according to the present invention will generally comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the proximal portions of the catheter bodies will typically be very flexible and suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques.

The distal portion of the catheters of the present invention may have a wide variety of forms and structures. In many embodiments, a distal portion of the catheter is more rigid than a proximal portion, but in other embodiments the distal portion may be equally as flexible as the proximal portion. One aspect of the present invention provides catheters having a distal portion with a reduced rigid length. The reduced rigid length can allow the catheters to access and treat tortuous vessels and small diameter body lumens. In most embodiments a rigid distal portion or housing of the catheter body will have a diameter that generally matches the proximal portion of the catheter body, however, in other embodiments, the distal portion may be larger or smaller than the flexible portion of the catheter.

A rigid distal portion of a catheter body can be formed from materials which are rigid or which have very low flexibilities, such as metals, hard plastics, composite materials, NiTi, steel with a coating such as titanium nitride, tantalum, ME-92®, diamonds, or the like. Most usually, the distal end of the catheter body will be formed from stainless steel or platinum/iridium. The length of the rigid distal portion may vary widely, typically being in the range from 5 mm to 35 mm, more usually from 10 mm to 25 mm, and preferably between 6 mm and 8 mm. In contrast, conventional catheters typically have rigid lengths of approximately 16 mm.

The side opening windows of the present invention will typically have a length of approximately 2 mm. In other embodiments, however, the side opening cutting window can be larger or smaller, but should be large enough to allow the cutter to protrude a predetermined distance that is sufficient to debulk material from the body lumen.

The catheters of the present invention can include a flexible atraumatic distal tip coupled to the rigid distal portion of the catheter. For example, an integrated distal tip can increase the safety of the catheter by eliminating the joint between the distal tip and the catheter body. The integral tip can provide a smoother inner diameter for ease of tissue movement into a collection chamber in the tip. During manufacturing, the transition from the housing to the flexible distal tip can be finished with a polymer laminate over the material housing. No weld, crimp, or screw joint is usually required.

The atraumatic distal tip permits advancing the catheter distally through the blood vessel or other body lumen while reducing any damage caused to the body lumen by the catheter. Typically, the distal tip will have a guidewire channel to permit the catheter to be guided to the target lesion over a guidewire. In some exemplary configurations, the atraumatic distal tip comprises a coil. In some configurations the distal tip has a rounded, blunt distal end. The catheter body can be tubular and have a forward-facing circular aperture which communicates with the atraumatic tip. A collection chamber can be housed within the distal tip to store material removed from the body lumen. The combination of the rigid distal end and the flexible distal tip is approximately 30 mm.

A rotatable cutter or other tissue debulking assembly may be disposed in the distal portion of the catheter to sever material which is adjacent to or received within the cutting window. In an exemplary embodiment, the cutter is movably disposed in the distal portion of the catheter body and movable across a side opening window. A straight or serrated cutting blade or other element can be formed integrally along a distal or proximal edge of the cutting window to assist in severing material from the body lumen. In one particular embodiment, the cutter has a diameter of approximately 1.14 mm. It should be appreciated however, that the diameter of the cutter will depend primarily on the diameter of the distal portion of the catheter body.

In exemplary embodiments, activation of an input device can deflect a distal portion of the catheter relative to the proximal portion of the catheter. Angular deflection of the distal portion may serve one or more purposes in various embodiments. Generally, for example, deflection of the distal portion increases the effective "diameter" of the catheter and causes the debulking assembly to be urged against material in a lumen, such as atherosclerotic plaque. In other embodiments, deflection of the distal portion may act to expose a debulking assembly through a window for contacting material in a lumen. In some embodiments, for example, activation of the input device moves the debulking assembly over a ramp or cam so that a portion of the rigid distal portion and flexible tip are caused to drop out of the path of the debulking assembly so as to expose the debulking assembly through the window. In some embodiments, deflection may both urge a portion of the catheter into material in a lumen and expose a tissue debulking assembly.

Some embodiments further help to urge the debulking assembly into contact with target tissue by including a proximal portion of the catheter body having a rigid, shaped or deformable portion. For example, some embodiments include a proximal portion with a bend that urges the debulking assembly toward a side of the lumen to be debulked. In other embodiments, one side of the proximal portion is less rigid than the other side. Thus, when tension is placed on the catheter in a proximal direction (as when pulling the debulking assembly proximally for use), one side of the proximal portion collapses more than the other, causing the catheter body to bend and the debulking assembly to move toward a side of the lumen to be debulked.

In exemplary embodiments, the debulking assembly comprises a rotatable cutter that is movable outside the window. By moving the cutter outside of the cutting window beyond an outer diameter of the distal portion of the catheter, the cutter is able to contact and sever material that does not invaginate the cutting window. In a specific configuration, the rotating cutter can be moved over the cam within the rigid, or distal, portion of the catheter body so that the cutting edge is moved out of the window. Moving the rotating cutter outside of the cutting window and advancing the entire catheter body distally, a large amount of occlusive material can be removed. Consequently, the amount of material that can be removed is not limited by the size of the cutting window.

As will be described in detail below, in some situations it is preferable to provide a serrated cutting edge, while in other situations it may be preferable to provide a smooth cutting edge. Optionally, the cutting edge of either or both the blades may be hardened, e.g., by application of a coating. A preferred coating material is a chromium based material, available from ME-92, Inc., which may be applied according to manufacturer's instructions. In some embodiments, the cutter includes a tungsten carbide cutting edge. Other rotatable and axially movable cutting blades are described in U.S. Pat. Nos. 5,674,232; 5,242,460; 5,312,425; 5,431,673; and 4,771,774, the full disclosures of which are incorporated herein by reference. In some embodiments, a rotatable cutter includes a beveled edge for removal of material from a body lumen while preventing injury to the lumen. In still other embodiments, a tissue debulking assembly may include alternative or additional features for debulking a lumen. For example, the debulking assembly may include, but is not limited to, a radio frequency device, an abrasion device, a laser cutter and/or the like.

The catheters of the present invention may include a monorail delivery system to assist in positioning the cutter at the target site. For example, the tip of the catheter can include lumen(s) that are sized to receive a conventional guidewire (typically 0.014" diameter) or any other suitable guidewire (e.g., having diameters between 0.018" and 0.032") and the flexible proximal portion of the catheter body can include a short lumen (e.g., about 12 centimeters in length). Such a configuration moves the guidewire out of the rigid portion so as to not interfere with the debulking assembly.

In other embodiments, however, the guidewire lumen may be disposed within or outside the flexible proximal portion of the catheter body and run a longer or shorter length, and in fact may run the entire length of the flexible portion of the catheter body. The guidewire can be disposed within lumen on the flexible portion of the catheter body and exit the lumen at a point proximal to the rigid portion of the catheter. The guidewire can then enter a proximal opening in the tip lumen and exit a distal opening in the tip lumen. In some embodiments, the catheter has a distal guidewire lumen on its flexible distal tip and a proximal guidewire lumen on its flexible body. For example, in some embodiments the distal lumen may have a length of between about 2.0 cm and about 3.0 cm and the proximal lumen may have a length of between about 10 cm and about 14 cm. In yet further embodiments, a distal tip guidewire lumen may be configured to telescope within a proximal guidewire lumen, or vice versa. A telescoping guidewire lumen may enhance performance of the catheter by preventing a guidewire from being exposed within a body lumen.

The present invention may optionally employ any of a wide variety of conventional radiopaque markers, imaging devices, and/or transducers. In exemplary embodiments, the catheters of the present invention can include a radiopaque distal portion and/or radiopaque markers disposed on a distal portion of the catheter body, such as proximal and distal of the cutting window, on the cam or ramp, so as to allow the user to track the position of the cutter, or the like. The catheters of the present invention will also be particularly useful with ultrasonic transducers, such as an IVUS, of a type which may be deployed linearly within the catheter body or circumferentially on the debulking assembly. Linear deployment will allow viewing along a discrete length of the catheter axis, preferably adjacent to the cutting point, usually over a length in the range from 1 mm to 30 mm, preferably 2 mm to 10 mm. Circumferentially deployed phased arrays may subtend a viewing arc in the range from 5° to 360°, usually from 180° to 360°. For imaging transducers located on cutting blades within a housing or second cutting element, the field of imaging will generally be limited by the dimensions of the aperture. In some cases, however, it might be possible to fabricate all or a portion of the cutter blade/housing out of an ultrasonically translucent material. A more complete description of suitable imaging catheters are described more fully in U.S. patent application Ser. No. 09/378,224, filed Aug. 19, 1999, and entitled "Atherectomy Catheter with Aligned Imager," now U.S. Pat. No. 6,299,622 B1, the complete disclosure of which is incorporated herein by reference. In addition to ultrasonic array transducers, the imaging devices of the present invention may comprise optical coherence tomography devices, such as described in U.S. Pat. No. 5,491,524, the full disclosure of which is incorporated herein by reference, as well as Huang et al. (1991) Science 254:1178-1181; Brezinski et al. (1997) Heart 77:397-403; and Brezinski et al. (1996) Circulation 93:1206-1213. In some instances, the present invention may also provide optical imaging using optical wave guides and the like.

Referring now to FIG. 1, a catheter 20 constructed in accordance with principles of the present invention comprises a catheter body 22 having a proximal portion 24 and a distal portion 26. Proximal portion 24 can be coupled to distal portion 26 with a connection assembly 27 to allow pivoting or deflection of distal portion 26 relative to proximal portion 24. A proximal end of the catheter body 22 can have a handle 40 for manipulation by a user, a luer for connection to an aspiration or fluid delivery channel, or the like.

A debulking assembly, such as a cutter 28, abrasive member, or the like, is disposed within a lumen 30 of the catheter body 22. The cutter 28 is typically rotatable within the distal portion 26 about an axis that is parallel to the longitudinal axis of the distal portion 26 of catheter 20 and axially movable along the longitudinal axis. The cutter 28 can access target tissue through a side opening window 32 which is typically large enough to allow the cutter 28 to protrude through and move out of the window 32 a predetermined distance. The cutter is coupled to a cutter driver 34 through a coiled drive shaft 36. Actuation of a movable actuator or other input device 38 can activate the drive shaft 36 and cutter, move cutter 28 longitudinally over a cam so as to deflect the distal portion and move the cutter 28 out of cutting window 32. Camming of the cutter 28 can cause the distal portion 26 to pivot or deflect relative to the proximal portion 24 so as to deflect and urge the cutter into the tissue in the body lumen.

In some embodiments, the distal portion 26 of the catheter may be moved to an angled or offset configuration from the longitudinal axis of the proximal portion 24 of the catheter and the cutter 28. In some embodiments, the cutter 28 can also be deflected off of the axis of the proximal and/or distal portion of the catheter. Moving the distal portion 26 to an angled/offset position may cause a portion of the catheter to urge against a target tissue, may expose the cutter 28 through the window 32 or both, in various embodiments.

In catheters 20 of the present invention, proximal portion 24 is typically relatively flexible and distal portion 26 is typically relatively rigid. Additionally, many embodiments include a flexible distal tip 42. The flexible proximal portion 24 of the catheter is typically a torque shaft and the distal portion 26 is typically a rigid tubing. The torque shaft 24 facilitates transportation of the catheter body 22 and cutter 28 to the diseased site. The proximal end of the torque shaft 24 is coupled to a proximal handle 40 and the distal end of the torque shaft is attached to the distal, rigid portion 26 of the catheter through the connection assembly 27. The drive shaft 36 is movably positioned within the torque shaft 24 so as to rotate and axially move within the torque shaft 24. The drive shaft 36 and torque shaft 24 are sized to allow relative movement of each shaft without interfering with the movement of the other shaft. The catheter body will have the pushability and torqueability such that torquing and pushing of the proximal end will translate motion to the distal portion 26 of the catheter body 22.

Referring now to FIG. 1A, a catheter 20 as in FIG. 1 may have a flexible proximal portion 24 which additionally includes urging means 25. As shown in FIG. 1A, urging means 25 may comprise a rigid bent or curved shape towards the distal end of proximal portion 24, which may help urge the cutter 28 or other debulking apparatus toward a wall of a body lumen to enhance treatment. Such a rigid bend increases the working range of the catheter by allowing the cutter to be urged into a lumen wall across a wider diameter lumen.

In other embodiments, urging means 25 may take many other suitable forms. For example, a similar result to the rigid bend may be achieved by including a rigid distal portion that is not permanently bent but that is more rigid on one side than on the opposite side of catheter body 22. Thus, when proximal tension is applied to the proximal portion 24, as when proximal force is applied to the debulking apparatus to expose the cutter 28 through the window 32, the urging means 25 (i.e., the rigid distal portion of proximal portion 24) will cause the catheter body 22 to bend toward the less rigid side. The less rigid side will typically be the same side as the window 32, so that the window 32 and/or the cutter 28 will be urged against a wall of a body lumen by the bend. In still other embodiments, a shaped element may be introduced into catheter body to act as urging means 25. Any suitable urging means is contemplated.

Figure 2:
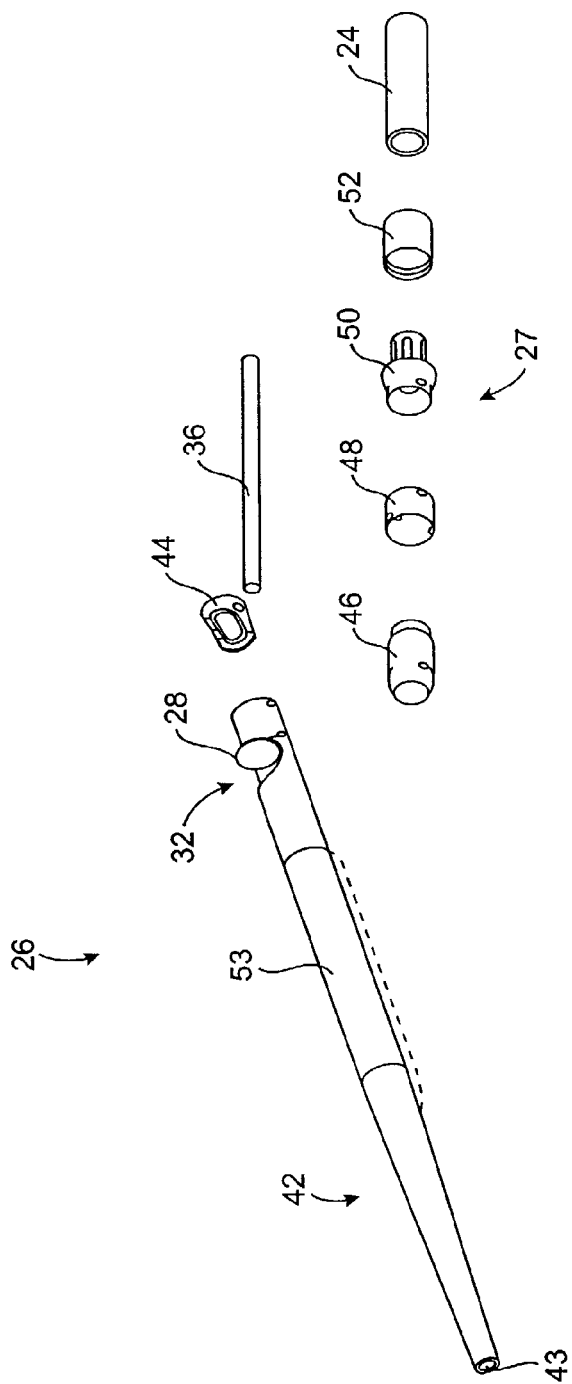
FIG. 2 is an exploded view of an exemplary distal portion of the debulking catheter of the present invention.

FIG. 2 illustrates an exploded view of a distal end of the catheter. In such embodiments, the catheter 10 includes a connection assembly 27, a rigid housing 26, a distal tip 42 that at least partially defines a collection chamber 53 for storing the severed atheromatous material, and a lumen that can receive the guidewire. The distal tip 42 can have a distal opening 43 that is sized to allow an imaging guidewire or conventional guidewire (not shown) to be advanced distally through the tip. In some embodiments, the distal tip 42 may also include a distal guidewire lumen (not shown) for allowing passage of a guidewire. For example, some embodiments may include a distal guidewire lumen having a length of between about 1.0 cm and about 5.0 cm, and preferably between about 2.0 cm and about 3.0 cm. Such a distal guidewire lumen may be used alone or in conjunction with a proximal guidewire lumen located on another, more proximal, portion of the catheter 20.

In embodiments including a distal guidewire lumen and a proximal guidewire lumen, the distal lumen may be configured to partially telescope within a portion of the proximal guidewire lumen, or vice versa. Such telescoping lumens may be used in embodiments where the distal portion 26 of catheter body 22 is movable relative to the proximal portion 24. A telescoping lumen may enhance performance of the catheter 20 by allowing a guidewire to be maintained largely within a lumen and to not be exposed within the body lumen being treated. Telescoping lumens may have any suitable diameters and configurations to allow for sliding or otherwise fitting of one lumen within another.

A ramp or cam 44 can at least partially fit within the distal portion 26. As will be described in detail below, in many embodiments proximal movement of the cutter 28 over the ramp 44, causes the deflection of the distal housing 26 and guides cutter 28 out of cutting window 32. (In other embodiments, a ramp may be used to deflect the distal portion without extending the cutter out of the window.) Attached to the ramp 44 is a housing adaptor 46 that can connect one or more articulation member 48 to the distal tip to create an axis of rotation of the distal portion 26. The housing adaptor 46 and articulation member 48 allow the distal end of the catheter to pivot and bias against the body lumen. In the illustrated embodiment there are only one housing adaptor 46 and one articulation member 48, but it should be appreciated that the catheters of the present invention can include, two, three, or more joints (e.g., axis of rotation), if desired. Moreover, the axes of rotation can be parallel or non-parallel with each other.

The catheter can also include a shaft adaptor 50 and collar 52 to couple articulation member 48 to the torque shaft 22. Shaft adaptor 50 can connect the housing to the torque shaft and collar 52 can be placed over a proximal end of the shaft adaptor and crimped for a secure attachment. It should be appreciated by one of ordinary skill in the art that that while one exemplary catheter of the present invention has the above components that other catheters of the present invention may not include more or fewer of the components described above. For example, some components can be made integral with other components and some components may be left out entirely. Thus, instead of having a separate ramp 44, the ramp may be integrated with the distal tip to direct the cutter out of the cutting window.

Figures 3A, 3B:
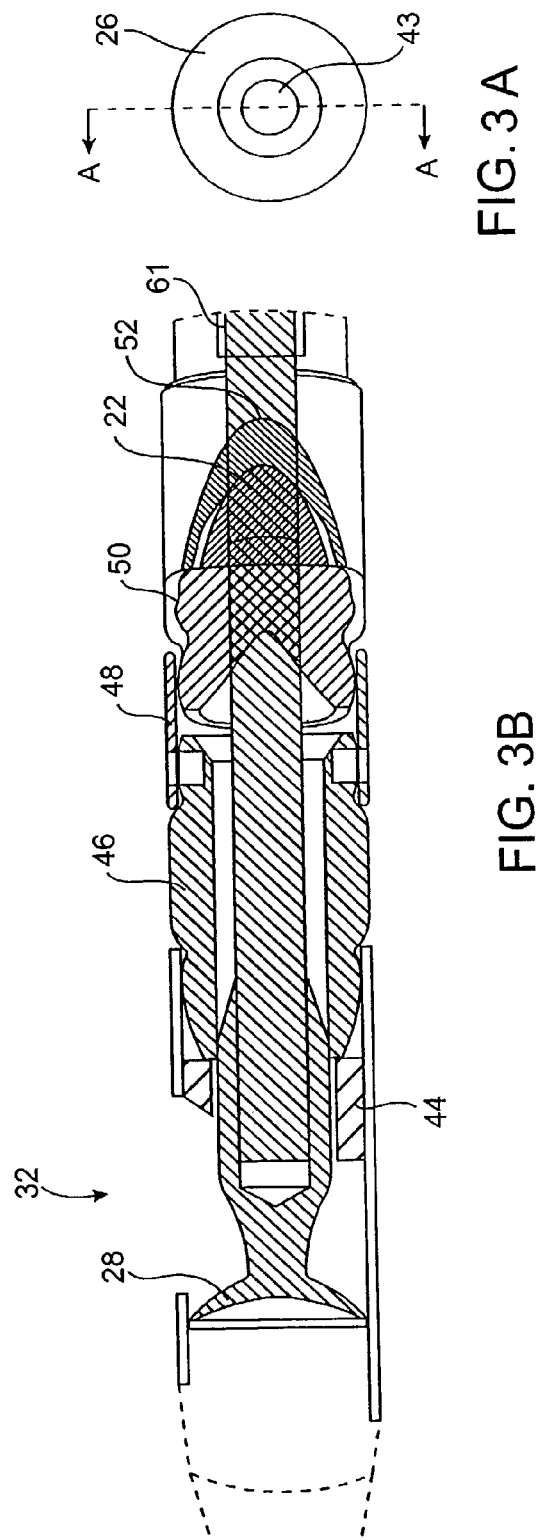
FIG. 3A is an end view of the distal portion of the debulking catheter of FIG. 1 in which the cutter is in a closed position in the catheter body.
FIG. 3B is a sectional view along Line A-A of FIG. 3A.

As shown in FIGS. 3-5, the cutters 28 of the present invention will generally be movable between two or more positions. During advancement through the body lumen, the cutter will generally be in a neutral position (FIGS. 3A and 3B) in which the cutter 28 is distal of cutting window 32. In some embodiments, an imaging device (not shown) can be coupled to cutter 28 so as to image the body lumen through cutting window 32 when cutter 28 is in the neutral position. Once the catheter 20 has reached the target site, the cutter 28 can be moved to an open position (FIGS. 4A and 4B) in which the cutter 28 is moved to a proximal end of the cutting window 32 and will extend out of the cutting window 32 a distance $L_1$ beyond an outer diameter D of the rigid portion 26. In most embodiments, in the open position, the cutter will have deflected the distal portion and the cutter's axis of rotation will generally be in line with connection assembly 27 but angled or offset from longitudinal axis of the distal portion of the catheter body.

Optionally, in some embodiments, cutter 28 can be moved to a packing position, in which the cutter is moved distally, past the neutral position, so as to pack the severed tissue into a distal collection chamber 53 (FIGS. 5A and 5B). It should be appreciated however, that while the exemplary embodiment moves the cutter to the above described positions, in other embodiments of the present invention the cutter can be positioned in other relative positions. For example, instead of having the neutral position distal of the cutting window, the neutral position may be proximal of the window, and the open position may be along the distal end of the cutting window, or the like.

Referring again to FIGS. 4A and 4B, the interaction of the components of the rigid distal portions 26 in one exemplary embodiment of the present invention will be further described. As shown in FIG. 4B, the cutting window 32 is typically a cutout opening in the distal portion 26. While the size of the cutting window 32 can vary, the cutting window should be long enough to collect tissue and circumferentially wide enough to allow the cutter to move out of the cutting window during cutting, but sized and shaped to not expel emboli into the vasculature. Cams or ramp 44 (shown most clearly in FIG. 4B) can be disposed in the distal portion of the catheter body to guide or otherwise pivot the cutter 28 out of the cutting window 32 as the cutter 28 is pulled proximally through tensioning of drive shaft 36.

A joint is located proximal to the cutting window 32 to provide a pivot point for camming of the distal portion 26 relative to the proximal portion 24. The bending at a flexible joint 49 is caused by the interaction of cams or ramps 44 with cutter 28 and the tensile force provided through drive shaft 36. In the exemplary configuration, the joint includes a housing adaptor 46 that is pivotally coupled to the distal rigid portion 26. As shown in FIGS. 4A and 4B, the resulting pivoting of the rigid distal portion 26 relative to the proximal portion causes a camming effect which urges the distal housing against the body lumen wall without the use of urging means (e.g., a balloon) that is positioned opposite of the cutting window. Thus, the overall cross sectional size of the catheter bodies can be reduced to allow the catheter to access lesions in smaller body lumens. In exemplary embodiments, the distal housing can deflect off of the axis of the proximal portion of the catheter typically between 0° degrees and 30° degrees, usually between 5° degrees and 20° degrees, and most preferably between 5° degrees and 10° degrees. The angle of deflection relates directly to the urge. Urge, however, does not necessarily relate to force but more to the overall profile of the catheter. For example, the greater the angle of deflection, the larger the profile and the bigger the lumen that can be treated. The ranges were chosen to allow treatment of vessels ranging from less than 2 mm to greater than 3 mm within the limits of mechanical design of the components. It should be appreciated however, that the angles of deflection will vary depending on the size of the body lumen being treated, the size of the catheter, and the like.

In some embodiments, the deflection of the distal portion 26 of the catheter urges the cutter into position such that distal advancement of the entire catheter body can move the rotating cutter through the occlusive material. Because the cutter is moved a distance $L_1$ beyond the outer diameter of the distal portion of the catheter and outside of the cutting window, the user does not have to invaginate the tissue into the cutting window. In some embodiments, for example, the cutter can be moved between about 0.025 mm and about 1.016 mm, and preferably between about 0.025 mm and about 0.64 mm, beyond the outer dimension of the distal housing. It should be appreciated that the cutter excursion directly relates to the depth of cut. The higher the cutter moves out of the cutting window the deeper the cut. The ranges are chosen around efficacy without risk of perforation of the body lumen.

Some embodiments of the catheter include a shuttle mechanism or other similar mechanism for temporarily locking the catheter in a cutting position. FIGS. 3C and 3D illustrate such an embodiment in the neutral, non-cutting position. Such embodiments generally include a shuttle member 45 and a shuttle stop member 42. The shuttle stop member 42 is typically disposed at an angle, relative to a longitudinal axis through the catheter. FIGS. 4C and 4D show the same embodiment in the cutting position. When the cutter 28 is moved into the cutting position in such embodiments, the shuttle member 45 falls into the shuttle stop member 42 and thus locks the debulking apparatus in a cutting position. To unlock the debulking apparatus, the cutter 28 may be advanced forward, distally, to release the shuttle member 45 from the shuttle stop member 42.

Some embodiments including a shuttle mechanism will also include two joints in catheter body 22. Thus, catheter body 22 will include a proximal portion 26, a distal portion 24 and a middle portion. When shuttle mechanism is activated to expose cutter 28 through window 32, the middle portion may orient itself at an angle, relative to the proximal and distal portions, thus allowing cutter to be urged towards a side of a lumen. Such a two-jointed configuration may provide enhanced performance of the catheter 20 by providing enhanced contact of the cutter 28 with material to be debulked from a body lumen.

Pushing the entire catheter across a lesion removes all or a portion of the lesion from the body lumen. Severed tissue from the lesion is collected by directing it into a collection chamber 53 in the tip via the cutter 28. Once the catheter and cutter 28 have moved through the lesion, the cutter 28 can be advanced distally to a "part off position" in which the cutter is moved back into the cutting window 32 (FIG. 3B). The tissue is collected as the severed pieces of tissue are directed into a collection chamber 53 via the distal movement of cutter 28 and catheter. The collection chamber 53 of the tip and distal portion 26 acts as a receptacle for the severed material, to prevent the severed occlusive material from entering the body lumen and possibly causing downstream occlusions. The cutter 28 can interact with the distal edge of the cutting window to part off the tissue and thereafter pack the severed tissue into collection chamber 53 (FIG. 3B). In exemplary embodiments, the driver motor can be programmed to stop the rotation of the cutter at the part off position so that the cutter 28 can move to a third position (FIG. 5B) and pack the material in the collection chamber in the tip without rotation. Typically, the collection chamber 53 will be large enough to allow multiple cuts to be collected before the device has to be removed from the body lumen. When the collection chamber is full, or at the user's discretion, the device can be removed, emptied and reinserted over the guidewire via a monorail system, as will be described below.

In various embodiments, enhancements to the collection chamber 53 may be included. For example, in some embodiments the collection chamber 53 may be configured to be partially or completely translucent or radiolucent and a portion of the catheter surrounding or adjacent to the window 32 will be radiopaque. This combination of radiolucent collection chamber 53 and radiopaque material adjacent window 32 will enhance the ability of a user to determine how full the collection chamber 53 is, because the fullness of the collection chamber will be directly related to the distance the cutter 28 can advance forward into the collection chamber 53. By facilitating the assessment of collection chamber filling, these embodiments will reduce the need for manually withdrawing the catheter to examine the collection chamber 53.

In some embodiments, the collection chamber 53 may connect to the rigid housing by means of interlocking components, which interlock with complementary components on the rigid housing. Such components may resemble a screw-in configuration, for example. Interlocking components will provide a stable connection between the collection chamber 53 and the rigid housing while not increasing the outer diameter of either the chamber 53 or the housing. Generally, collection chamber 53 may be given any suitable configuration, shape or size. For example, collection chamber 53 in FIGS. 6-8 has a helical configuration. Alternatively, collection chamber 53 may include a series of circular members, straight linear members, one solid cylindrical or cone-shaped member or the like.

Figure 6:
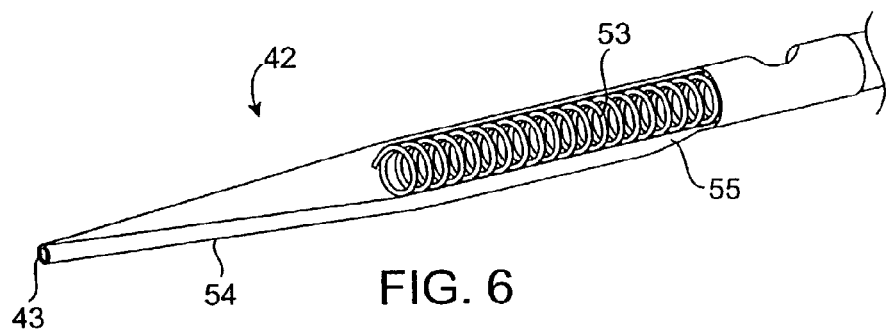
FIGS. 6 to 8 illustrate a monorail delivery system of the present invention.
Figure 7:
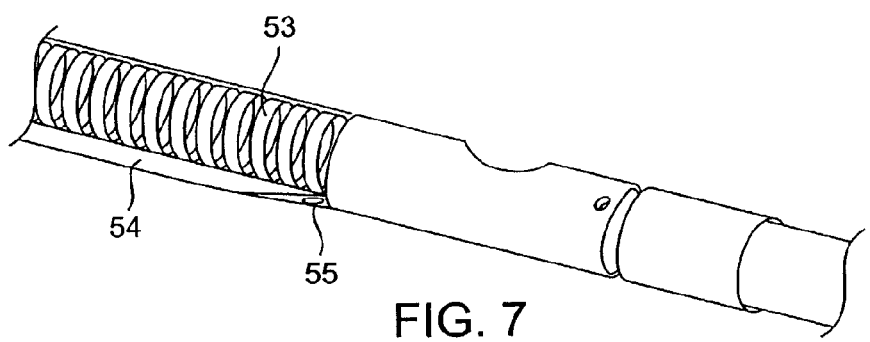
Figure 8:
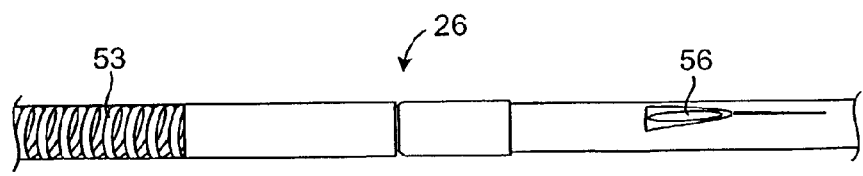

FIGS. 6 through 8 illustrate one exemplary monorail delivery system to assist in positioning the cutter 28 at the target site. For example, tip 42 of the catheter can include a lumen 54 having a distal opening 43 and a proximal opening 55 that is sized to receive a guidewire, having a diameter of about 0.014 in., about 0.018 in., about 0.032 in. or any other suitable diameter.

As shown in FIG. 8, the flexible proximal portion of the catheter body may also include a short lumen 56 (e.g., about 12 centimeters in length). In some embodiments, however, the guidewire lumen 56 may be disposed within or outside the flexible proximal portion of the catheter body and run a longer or shorter length, and in fact may run the entire length of the flexible portion 24 of the catheter body. In use, the guidewire can be disposed within lumen 56 on the flexible portion of the catheter body and exit the lumen at a point proximal to the rigid portion 26 of the catheter. The guidewire can then re-enter a proximal opening 55 in the tip lumen 54 and exit through distal opening 43 in the tip lumen. By moving the guidewire outside of the rigid portion 26 of the catheter body, the guidewire will be prevented from tangling with the cutter 28. Typically, tip lumen 54 will be disposed along a bottom surface of the tip and the lumen 56 will be disposed along a side of the proximal portion 22 of the catheter body so that the guidewire will be in a helical configuration. In various embodiments, the tip lumen 54 and the proximal lumen 56 can have any suitable combination of lengths. For example, in one embodiment the tip lumen 54 may have a length between about 1 cm and about 5 cm, more preferably between about 2 cm and about 3 cm, and the proximal lumen may have a length of between about 8 cm and about 20 cm, more preferably between about 10 cm and about 14 cm.

Figure 22:
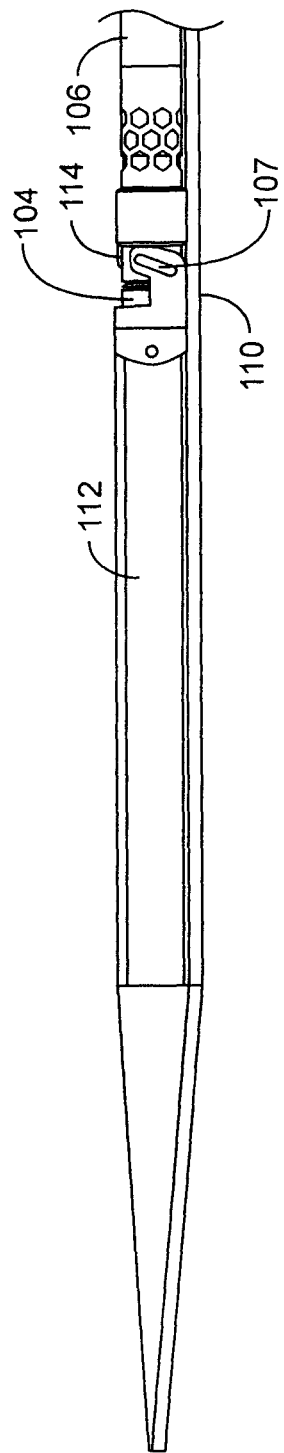
FIG. 22 shows the device of FIG. 21 with the cover in a stored position.
Figure 23:
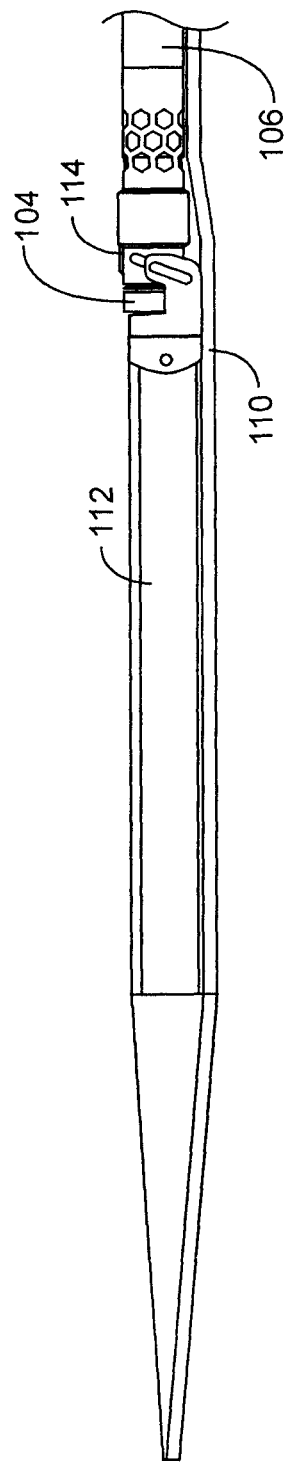
FIG. 23 shows the device of FIG. 21 with the cover in a working position which exposes part of the rotatable cutting element.

Referring now to FIGS. 22A and 22B, some catheters 120 of the present invention include a proximal guidewire lumen 126 coupled with the proximal portion of the catheter body 123, and a telescoping distal guidewire lumen 124 coupled with either the distal tip 122, part of the distal portion of the catheter body, or both. The telescoping lumen 124 will typically be attached to the tip 122 or a distal portion, but will also include an unattached portion 121, which will not be directly attached to any part of the catheter body. This unattached portion 121 (or "free floating lumen") protects a guidewire from contacting a body lumen in which the device is used and also allows the device to be moved more freely, without bending or kinking the guidewire. The telescoping guidewire 124 extends within the proximal lumen 126 at the distal opening 127 of proximal lumen 126. Again, the telescoping feature allows for movement of the catheter body while preventing or reducing bending of the guidewire. For example, in some embodiments catheter 120 allows for deflection of distal tip 122 and the distal portion of the catheter 120 relative to the proximal portion 123, for example by movement about a pivot point 129. Telescoping distal lumen 124 and proximal lumen 126 allow for this movement by allowing distal lumen 124 to telescope within proximal lumen 126. At the same time, distal lumen 124 protects a guide wire from exposure to a body lumen and/or bodily fluids.

Any suitable configurations and sizes of distal lumen 124 and proximal lumen 126 are contemplated. For example, in one embodiment distal lumen 124 may telescope within proximal lumen 126 by a distance of approximately 1 cm. Furthermore, a telescoping lumen 124 may be longer than distal lumens in other embodiments. For example, telescoping lumen 124 may have a length of between about 2 cm and about 10 cm, and preferably between about 5 cm and about 8 cm. As is apparent from the drawing figures, the outer diameter of telescoping distal lumen 124 is configured to fit within the inner diameter of proximal lumen 126. Generally, any combination of sizes, lengths, diameters and shapes of distal lumen 124 and proximal lumen 126 may be used, to allow telescoping of one into another.

The catheters of the present invention can include radiopaque markers so as to allow the user to track the position of the catheter under fluoroscopy. For example, as already described, a point or area around or adjacent to the window may be made radiopaque. In other embodiments, the rigid distal portion 26 can be radiopaque and radiopaque markers can be disposed on the flexible shaft. Typically, the markers 59 will be disposed along the top, proximal to the cutting window, and on the bottom of the catheter to let the user know the position of the cutter and cutting window relative to the target site. If desired, the top and bottom markers can be different shaped so as to inform the user of the relative orientation of the catheter in the body lumen. Because the guidewire will form a helix in its transition from lumen 56 to tip lumen 54, the user will be able to view the top and bottom radiopaque markers 59 without interference from the guidewire. Some embodiments of the catheter can also include a radiopaque cutter stop 61 (FIG. 3B) that is crimped to driveshaft 36 proximal of the cutter that moves with the cutter so as to let the user know when the cutter is in the open position.

FIGS. 9A through 11D show some exemplary embodiments of the cutter 28 of the present invention. The distal portion 60 of the rotatable cutter 28 can include a serrated knife edge 62 or a smooth knife edge 64 and a curved or scooped distal surface 66. The distal portion 60 may have any suitable diameter or height. In some embodiments, for example, the diameter across the distal portion 60 may be between about 0.1 cm and about 0.2 cm. A proximal portion 68 of the cutter 28 can include a channel 70 that can be coupled to the drive shaft 36 that rotates the cutter. As shown in FIGS. 10A-10C, some embodiments of the cutters can include a bulge or bump 69 that is provided to interact with a stent so as to reduce the interaction of the cutting edge with the stent. In any of the foregoing embodiments, it may be advantageous to construct a serrated knife edge 62, a smooth knife edge 64, or a scooped distal surface 66 out of tungsten carbide.

Figure 11A:
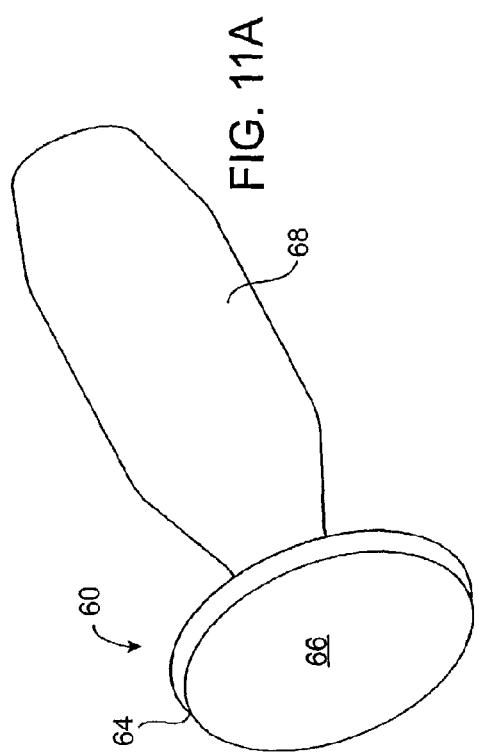
FIG. 11A is a perspective view of another in-stent restenosis cutter of the present invention.
Figure 11C:
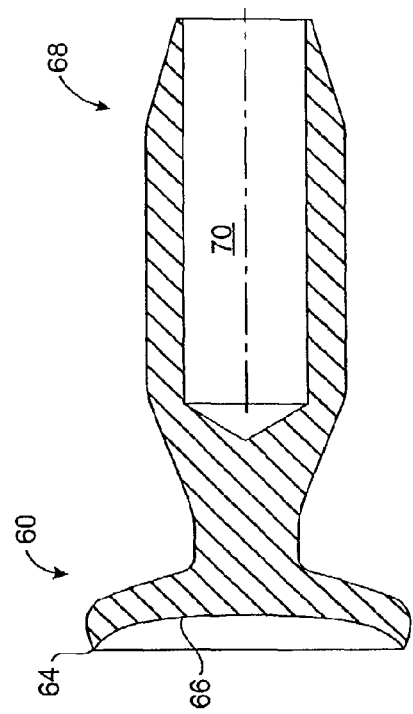
FIG. 11C is a sectional view of the cutter along Line C-C of the cutter of FIGS. 11A and 11B.
Figure 11B:
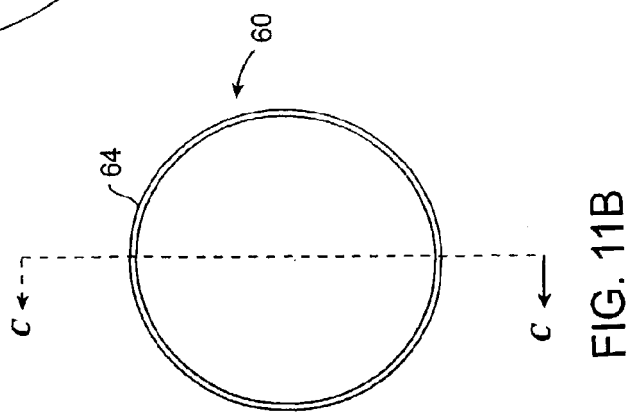
FIG. 11B is an end view of the cutter of FIG. 11A.
Figure 11D:
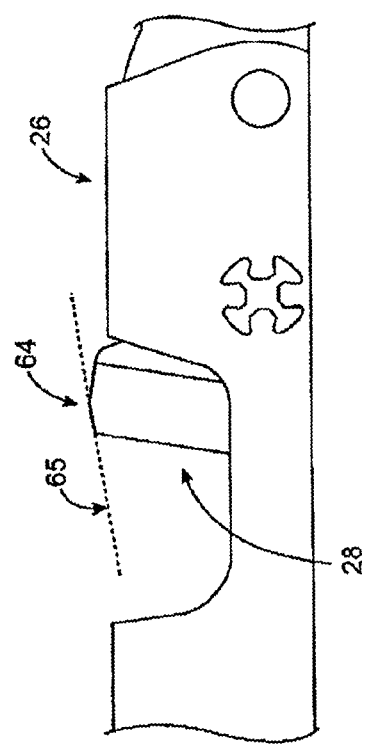
FIG. 11D is a side view of another embodiment of a cutter, shown partially within a catheter body.

Another embodiment of a cutter 28 suitable for use in the present invention is shown in side view within a catheter body distal portion 26 in FIG. 11D. In this embodiment, the cutter 28 has a beveled edge 64, made of tungsten carbide, stainless steel, titanium or any other suitable material. The beveled edge 64 is angled inward, toward the axis of rotation (or center) of the cutter 28, creating a "negative angle of attack" 65 for the cutter 28. Such a negative angle of attack may be advantageous in many settings, when one or more layers of material are desired to be debulked from a body lumen without damaging underlying layers of tissue. Occlusive material to be removed from a vessel typically has low compliance and the media of the vessel (ideally to be preserved) has higher compliance. A cutter 28 having a negative angle of attack may be employed to efficiently cut through material of low compliance, while not cutting through media of high compliance, by allowing the high-compliance to stretch over the beveled surface of cutter 28.

Figure 12:
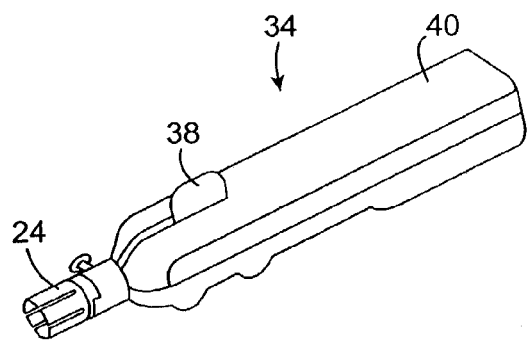
FIG. 12 illustrates a proximal handle and cutter driver of the present invention.
Figure 13:
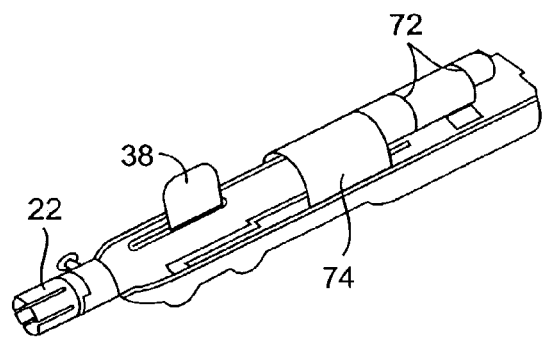
FIG. 13 illustrates a cutter driver with a handle cover removed.
Figure 14:
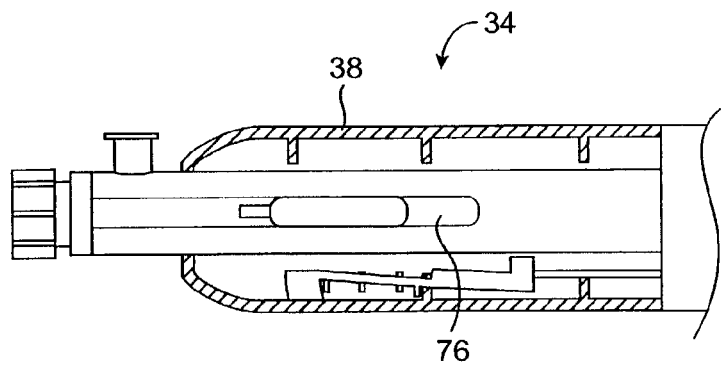
FIGS. 14 to 16 illustrate three positions of the lever for controlling the cutter.

FIGS. 12 through 16 illustrate an exemplary cutter driver 34 of the present invention. As shown in FIGS. 12 and 13, cutter driver 34 can act as the handle for the user to manipulate the catheters 20 of the present invention as well as a power source. Typically, the cutter drivers 34 of the present invention include a single input device, such as a lever 38 that controls the major operations of the catheter (e.g., axial movement to cause urging, rotation to cause cutting, and axial movement for packing). As shown in FIGS. 13 and 14, cutter driver 34 includes a power source 72 (e.g., batteries), a motor 74, a microswitch 76 for activating motor 74, and a connection assembly (not shown) for connecting the drive shaft 36 to the driver motor 74. In some embodiments, the drive motor can rotate drive shaft 36 between 1,000 rpm and 10,000 rpm or more, if desired.

Figure 15:
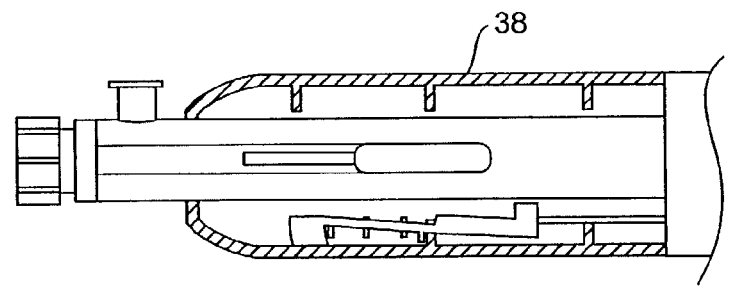
Figure 16:
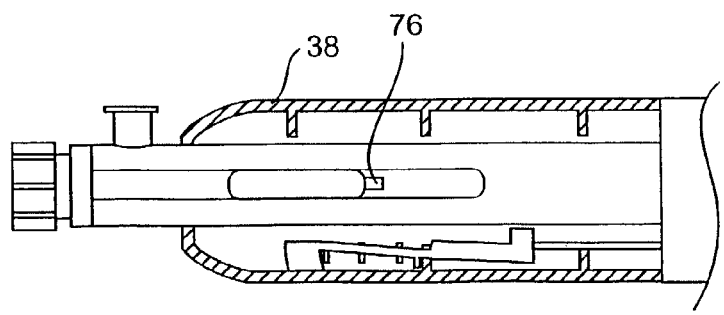

FIGS. 14 through 16 illustrate one exemplary method of operating cutter driver 34. In use, the catheter will be delivered to the target site with cutter driver unattached and the cutter in the neutral position (FIG. 3B). The cutter driver can be attached with the urge lever 38 in a neutral position (FIG. 14), which indicates that the cutter is closed, but not in a packing position. The user can then move the catheter (and cutter driver unit, if desired) to position the distal portion 26 of the catheter adjacent the target tissue. As shown in FIG. 15, to activate the rotation of the cutter, the urge lever 38 can be moved proximally from the neutral position to move the cutter proximally and out of cutting window 32 (FIG. 4B) and simultaneously depressing microswitch 76 to activate motor 74. At the end of the cutting procedure, as shown in FIG. 16, the user can push urge lever 38 completely forward to a distal position to push the cutter into a packing position (FIG. 5B). After the urge lever passes the middle of the travel, the microswitch 76 can be released so as to deactivate the cutter before reaching the packing position such that packing can occur without the cutter rotating. It should be appreciated, while the figures illustrate the use of an urge lever or thumb switch as an input device, the present invention can use other type of input devices, such as labeled buttons (e.g., close window, debulk tissue, and pack), or the like.

Advantageously, cutter driver 34 provides an automatic on/off control of the cutter 28 that is keyed to the position of the cutter. Such a configuration frees the user from the complicated task of remembering the sequence of operations to activate and deactivate the rotation and axial movement of the cutter.

While the cutter driver 34 is illustrated as a disposable battery powered unit, it should be appreciated that in other embodiments, the cutter driver can use other power sources to control the cutter driver. It should further be appreciated that other cutter drivers can be used with the present invention. While not preferred, it is possible to have separate controls to control the axial movement of the cutter and the rotation of the cutter.

Figure 17:
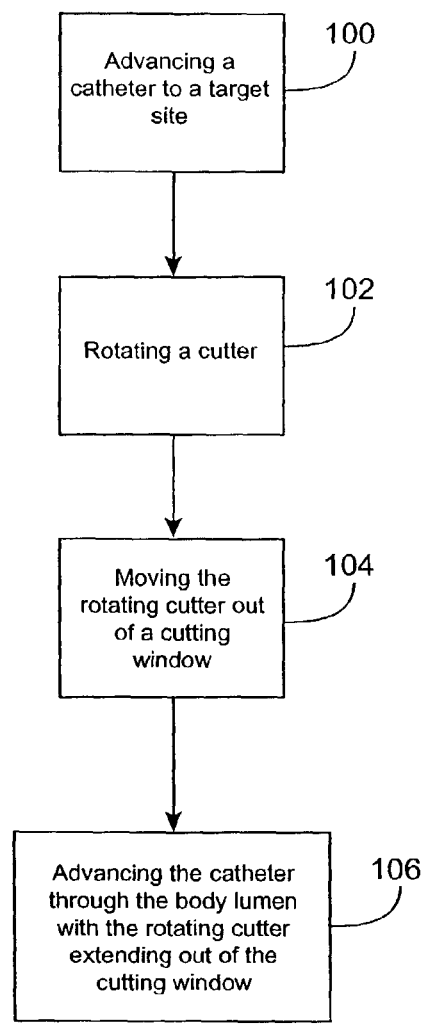
FIG. 17 is a simplified flow chart illustrating a method of the present invention.

Some exemplary methods of the present invention will now be described. One method of the present invention comprises delivering a catheter to a target site in the body lumen. A distal portion of the catheter can be deflected relative to a proximal portion of the catheter to expose a tissue debulking device in the catheter. The body lumen can be debulked with the exposed debulking device. Specifically, as shown schematically in FIG. 17, one specific method comprises advancing a catheter to a target site (Step 100). A cutter can be rotated and moved out of the cutting window (Steps 102, 104). Preferably, a distal portion of the catheter can be pivoted or deflected so as to position the cutter adjacent the target material. Thereafter, the catheter and the rotating cutter can be moved through the body lumen to remove the target material from the body lumen (Step 106).

As shown in FIGS. 18 and 19, the catheter can be percutaneously advanced through a guide catheter or sheath and over a conventional or imaging guidewire using conventional interventional techniques. The debulking catheter 20 can be advanced over the guidewire and out of the guide catheter to the diseased area. As shown in FIG. 18, the window 32 will typically be closed (with the cutter or other debulking device 28 in a first, distal position). As shown in FIG. 19, catheter 20 will typically have at least one hinge or pivot connection to allow pivoting about one or more axes of rotation to enhance the delivery of the catheter into the tortuous anatomy without dislodging the guide catheter or other sheath. The cutter can be positioned proximal of the lesion. Optionally, a transducer, IVUS, or other imaging assembly can be used to verify the position of the debulking catheter.

Once the position of the catheter is confirmed, the cutter 28 will be retracted proximally and moved out of cutting window 32 to its second, exposed position. In some embodiments, movement of the cutter can deflect the distal portion of the catheter to increase the profile of the catheter at the target area. Movement of the cutter is typically caused by proximal movement of lever 38 and tensioning of drive shaft 36. Movement of the lever can be scaled to any desired ratio or a direct 1:1 ratio of movement between the handle and cutter. When the cutter is moved proximally it contacts ramp or cam surfaces so as to guide the cutter up and at least partially out of the cutting window 32. Additionally, as shown by arrow 80, the distal portion of catheter body 26 rotates about the joint 49 to provide an urging force for the cutter (and catheter body) to move toward the diseased area.

Thereafter, as shown by arrow 82 the operator can move the entire catheter body 22 through the lesion to dissect the tissue. As the cutter 28 and catheter body 22 are advanced distally through the lesion, tissue that is trapped between the cutting edge 52 and the cutting window 32 is severed from the body lumen. To part off the tissue, the operator can stop pushing the device distally and the cutter can be advanced distally inside the cutting window by advancing the handle 38. During the distal movement of the cutter, the cutter 28 rides back over the ramps 44 and directs the cutter back inside of the cutting window 32. Such movement causes the distal portion 26 of the catheter to move in line with the cutter and proximal portion 24 (FIG. 5B). When the cutter has moved to its distal position, the cutter parts off the severed tissue and urges the severed tissue inside of a collection chamber 53 in the distal tip 42. Optionally, after the cutter 28 has parted off the tissue, the lever 38 and thus the non-rotating cutter 38 can be advanced distally to pack the tissue into the collection chamber 53 (FIG. 5B). Use of the cutter to pack the severed tissue will allow the operator multiple specimens to be collected prior to removing the catheter 20 from the body lumen. When it is determined that the collection chamber is full, the catheter can be removed from the body lumen and the collection chamber can be emptied.

Figure 20:
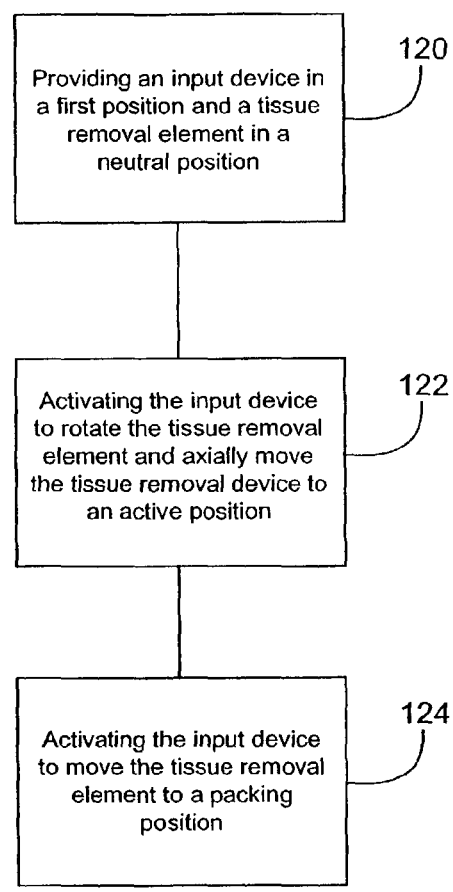
FIG. 20 schematically illustrates another method of the present invention
Figure 21:
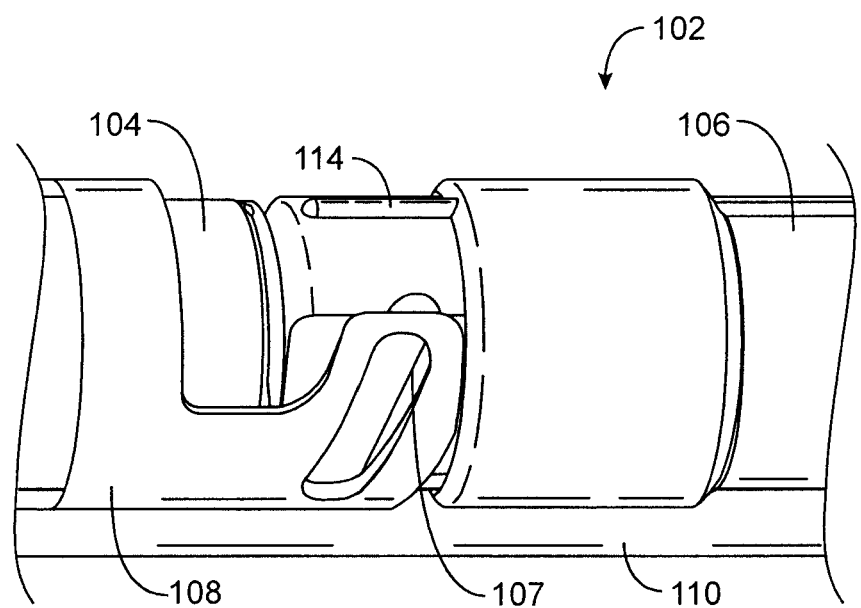
FIG. 21 shows another device for cutting tissue with the device having a movable cover.

In another method of the present invention, as shown in FIG. 20, an input device is disposed in a first position to position a tissue removal element in a neutral position (Step 120). The input device is activated to rotate the tissue removal element and to axially move the tissue removal device to an active position (Step 122). The input device can then be activated again to move the tissue removal element to a packing position (Step 124). In an exemplary embodiment, the input device is a lever or thumb switch that can be moved to correspond to the movement of a cutting element on the catheter. Thus, as the lever is moved proximally, the cutter is rotated and moved proximally to an open position. When the lever is moved to a distal position, the rotation of the cutter can be stopped and the cutter can be moved distally to pack severed tissue into a collection chamber.

Referring to FIGS. 21-24, still another device 102 for cutting and/or removing material is shown. The device 102 has a cutting element 104 which may be any suitable cutting element 104 such as those described herein. The device 102 has an elongate body 106 and a visualization element 114 coupled to the body 106. A cover or tip 108 is positioned at the distal end of the device 102. The cover 108 is movable from the stored position of FIGS. 21 and 22 to the working position of FIG. 23 in which at least part of the cutting element 104 is exposed The cover 108 may be movable relative to the elongate body 106 in any suitable manner. For example, the cover 108 and body 106 may engage one another with a slot and pin engagement 107 so that the cover 108 translates linearly relative to the body 106. The cover 108 may be naturally biased or held in the stored position with the user actuating the device to move the cover 108 to the working position. For example, the cover 108 may be coupled to a lumen 110, such as a guidewire lumen, with the user tensioning, or even compressing, the lumen 110 and/or body 106 to move the cover 108 to the working position. The cover 108 has a longitudinal axis which may remain substantially parallel to the longitudinal axis of the elongate body 106. Furthermore, the cover 108 may be movable to a number of different positions which expose varying amounts of the cutting element 104 so that the depth of cut may be selected or varied by the user. The cover or tip 108 may have a recess or cavity 112 in which material to be removed is held as is described herein.

The visualization element 114 may be any suitable visualization element such as a fiberoptic and lens or an ultrasound element. The visualization element 114 may be movable or fixed relative to the body 106. The visualization element 114 is positioned on a radially outer, and preferably outermost, portion of the body 106 so that the element 114 may be pressed against or moved adjacent to the tissue of interest. This may provide advantages when using certain types of visualization elements 114 such as optical elements which may emit or receive energy which is partially absorbed by blood or other fluids present. Various examples of a suitable visualization element are described in U.S. Pat. Nos. 6,191,862, 6,445,939, 6,134,003, 5,459,570 and 5,321,501 which are hereby incorporated by reference.

Figure 24:
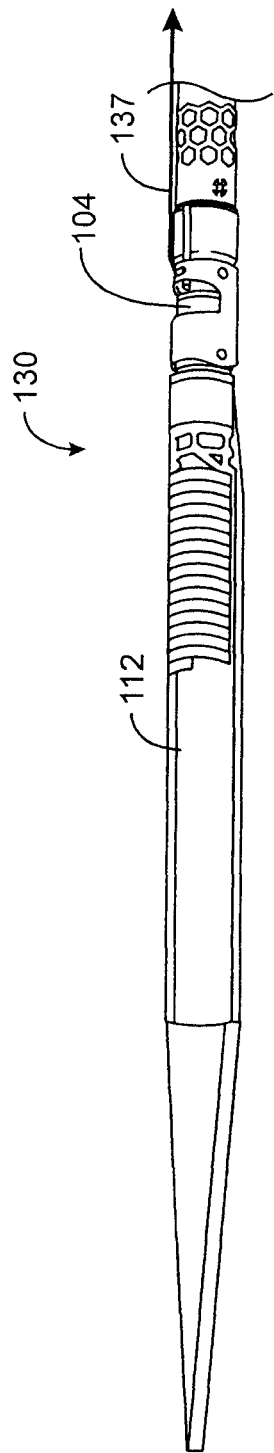
FIG. 24 shows still another device for cutting tissue having two pivot points on opposite sides of the cutting element.
Figure 25:
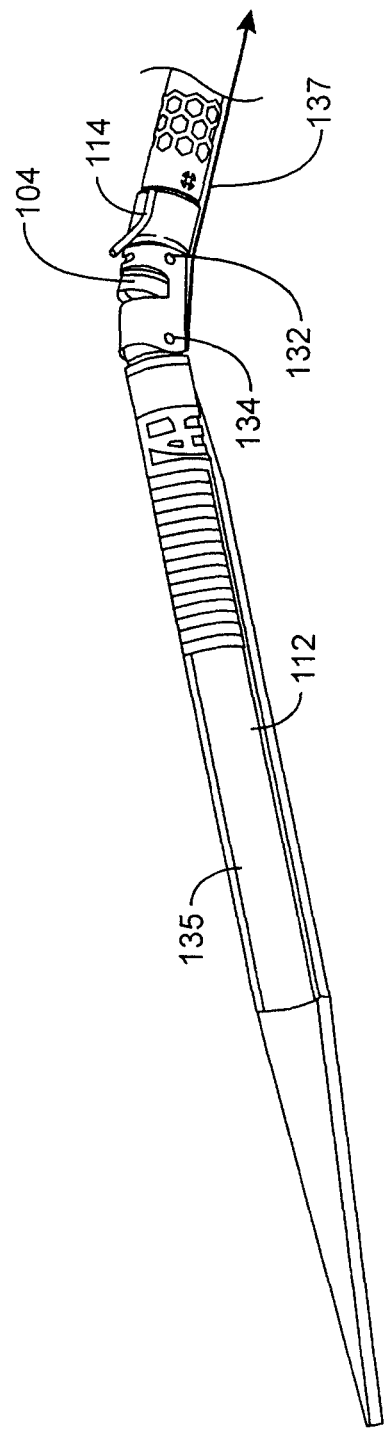
FIG. 25 shows the device of FIG. 24 after articulating the device at the pivot points to put the cutting element in a cutting position.

Referring to FIGS. 24 and 25, still another device 130 for cutting and/or removing material is shown wherein the same or similar reference numbers refer to the same or similar structure. The device 130 may be used to cut or remove material from a vascular location using any method described herein. The device 130 has the cutting element 104 which may be coupled to the torque transmitting element extending through the elongate body 106. A first pivot point 132 and a second pivot point 134 are positioned on opposite sides of the cutting element 104. When moving to the working position of FIG. 25, the cutting element 104 moves into engagement with the tissue to be cut or removed. The device 130 may also have the visualization element 114 positioned on the radially outermost part of the device 130. The visualization element may be moved from the stored position of FIG. 24 to the working position of FIG. 25. The device 130 has a tip 135 which has a recess or cavity 112 or other structure to receive material to be removed. The device 130 may be naturally biased toward the working or stored position with the other position being created by tensioning a pull wire 137 on one or the other side of the device 130.

Figure 26A:
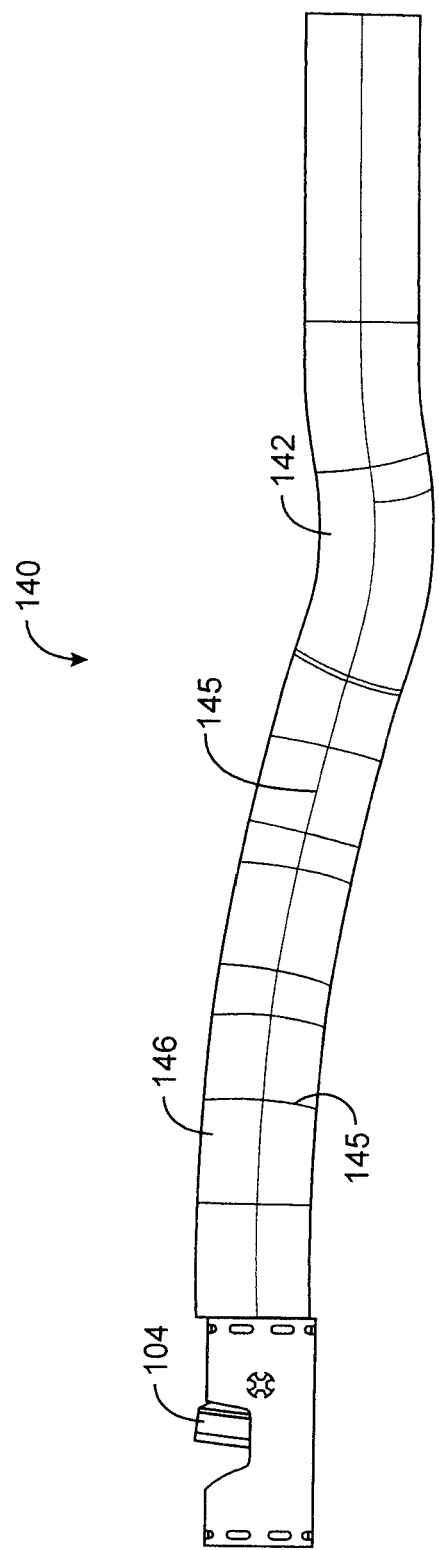
FIG. 26A is a side view of the elongate body or shaft forming a helical shape.
Figure 26B:
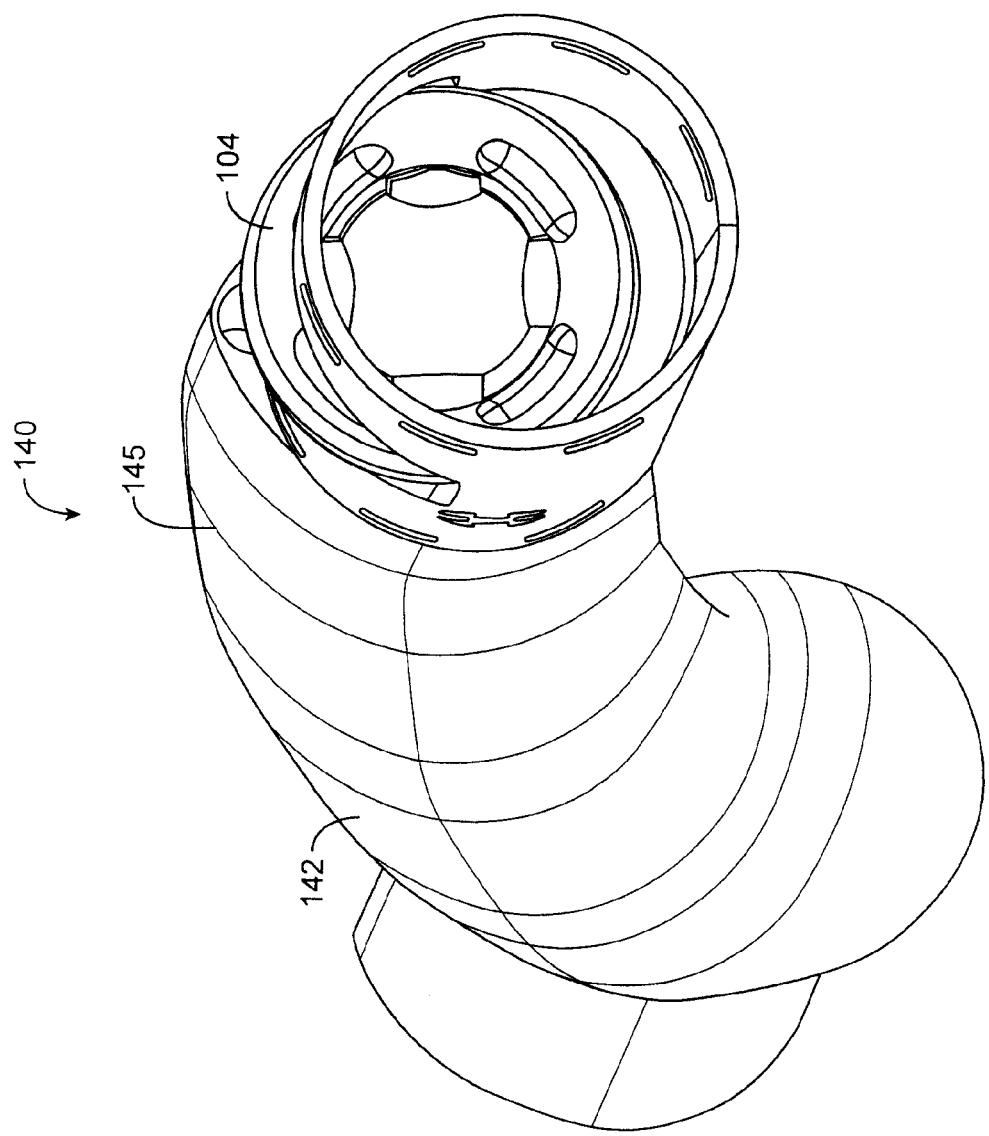
FIG. 26B is a perspective view looking at the distal end of the device.
Figure 27A:
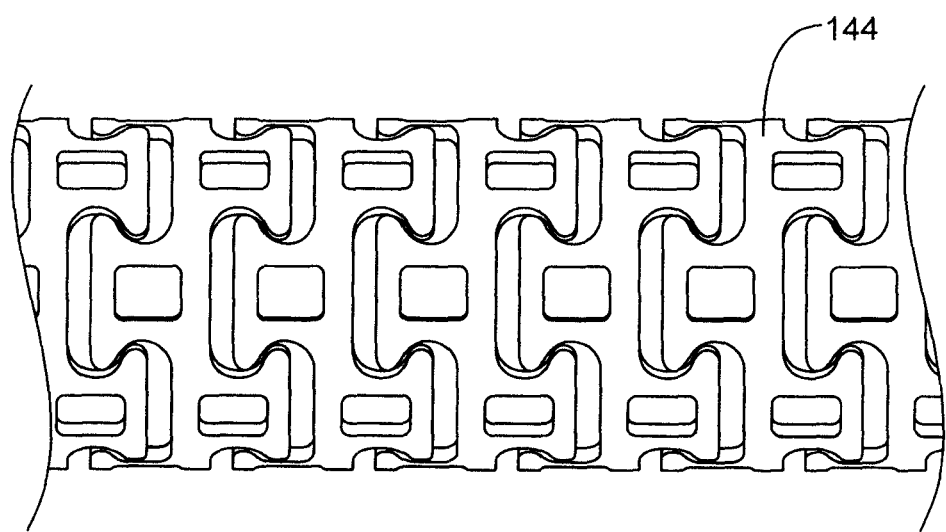
FIG. 27A shows a tube which forms part of the elongate body of FIG. 26 in a straight configuration.
Figure 27B:
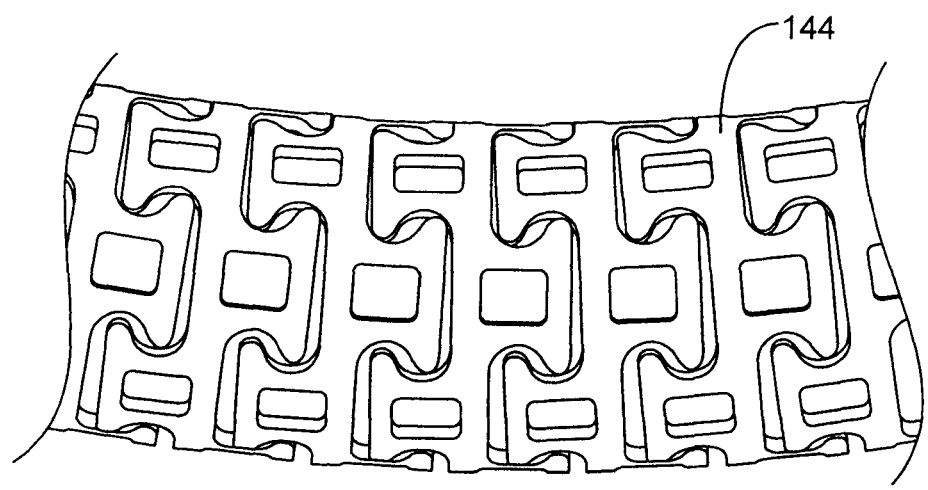
FIG. 27B shows the tube of FIG. 27A in a bent configuration.

Referring to FIGS. 26A and 26B, another device 140 is shown having an elongate body 142 which is deformable to a generally helical shape. The elongate body 142 is moved to the deformed or helical shape to help stabilize the device 140 within the vessel. Stabilization of the device 140 may be particularly helpful when moving the entire device 140 through the vessel when removing material as described herein. The helical shape of the body may help to stabilize the device, depending upon the particular shape of the vasculature, and may specifically help resist or reduce twisting of the device 140 within the vasculature as the device is advanced during cutting. The helical shape may be formed in any suitable manner. Referring to FIGS. 27A and 27B, for example, a tube 144 may be cut with a pattern which naturally forms the helical shape when a compressive force is applied to the tube 144. The tube 144 is contained in a sheath 146 which holds the tube 144 but permits the tube 144 to deform as necessary. As can be appreciated from FIGS. 26A and 26B, the helical shape may be somewhat subtle. Surface lines 145 have been added for clarity in visualizing the shape of the body 142. In one embodiment, the diameter of the body 142 is 1.0 to 2.5 mm while the diameter of the helical shape is about 2.0 to 7.5 mm. In still another aspect, the helical shape has less than 360 degrees of rotation over it's length and preferably about 180 degrees. The deformed part of the elongate body 142, 152 may be relatively long. For example, the deformed part may be at least 1 cm and may even be at least 2 cm when measured in a relaxed or straightened configuration. Of course, the elongate body 142 which may also be deformed to a generally S-shape rather than helical shape.

The shaft or body of FIGS. 26A and 26B may be used with any of the devices or methods described herein. For example, the helical body 142 may be used with the device 102 of FIGS. 21-23. Initial compression of the tube 144 may cause the body 142 to assume the helical shape. Continued compression of the tube 144 displaces the tip or cover 108 to expose the cutting element. The entire device 102 may then be moved through the vessel to cut a continuous piece of material which is directed into the recess or cavity 112 in the cover 108. Thus, it can be appreciated that many combinations are within the scope of the present invention with any of the working ends of the device being used with any of the shafts or elongate bodies.

Figure 28:
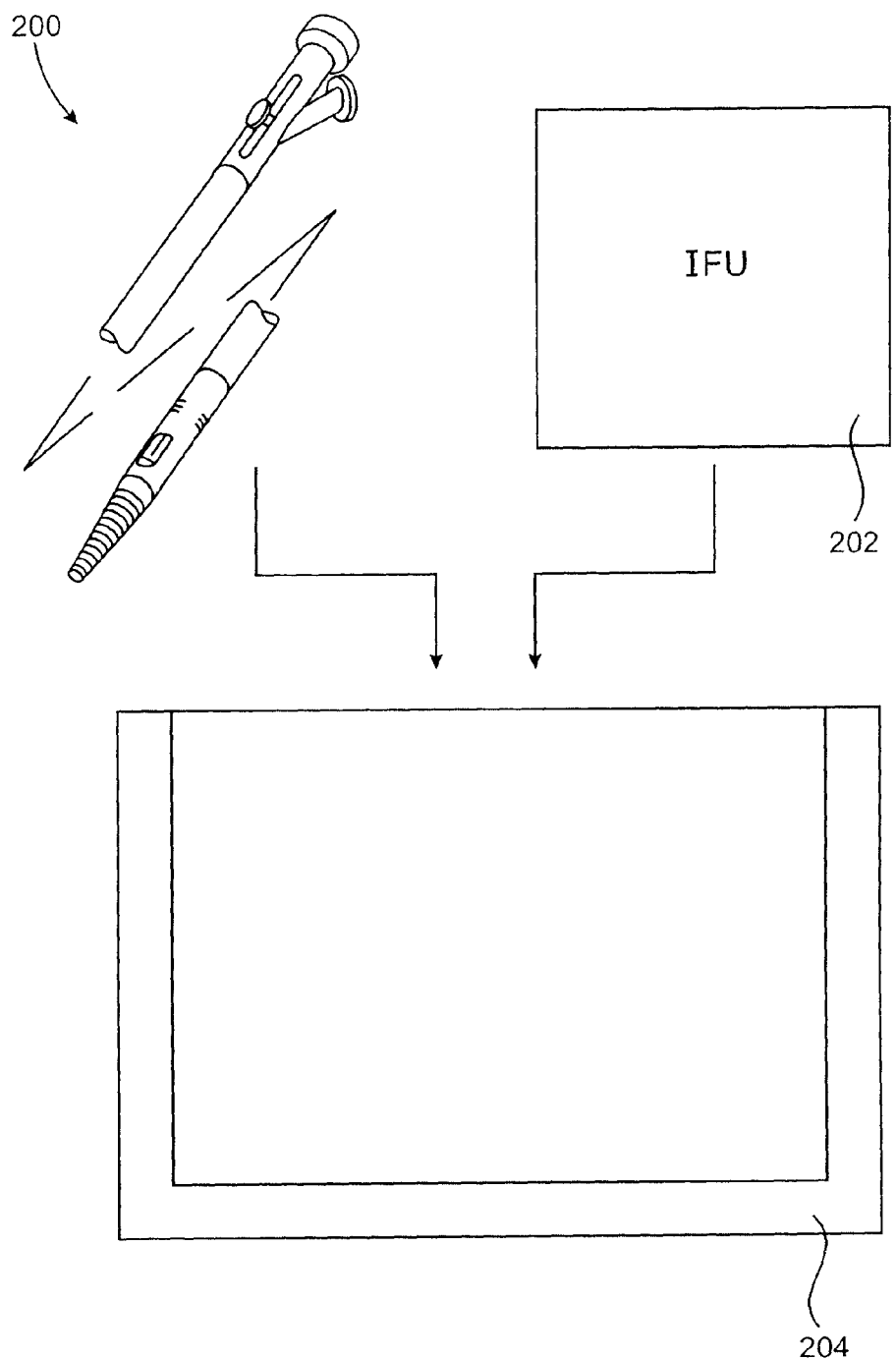
FIG. 28 illustrates a kit of the present invention.

Referring now to FIG. 28, the present invention will further comprise kits including catheters 200, instructions for use 202, and packages 204. Catheters 200 will generally be as described above, and the instruction for use (IFU) 202 will set forth any of the methods described above. Package 204 may be any conventional medical device packaging, including pouches, trays, boxes, tubes, or the like. The instructions for use 202 will usually be printed on a separate piece of paper, but may also be printed in whole or in part on a portion of the packaging 204.

While all the above is a complete description of the preferred embodiments of the inventions, various alternatives, modifications, and equivalents may be used. For example, while preferred cutters are moved proximally to move the cutter out of the cutting window, alternative embodiments may move the cutter distally to move the cutter out of the cutting window. Additionally, while most embodiments employ a cutter that extends out beyond the outer diameter of the cutting window, it may be possible to incorporate a cutter that stays within the diameter catheter body. Additionally, in some embodiments, the debulking assembly may be exposed through the window without causing a deflection of the distal portion of the catheter. Moreover, instead of having a distal tip that is rotatable relative to the proximal portion of the catheter, the catheter can include a shape memory material such that the catheter forms a jog or a pre-bent shape when it reaches its target area.

Although the foregoing invention has been described in detail for purposes of clarity of understanding, it will be obvious that certain modifications may be practiced within the scope of the appended claims.

What is claimed is:

1. A device for cutting tissue, comprising:
an elongate body having a distal and proximal ends and a longitudinal axis;
a rotatable cutting element, the rotatable cutting element being coupled to a torque transmitting element which extends through the elongate body; and
a movable cover having distal and proximal ends and a longitudinal axis, the proximal end of the movable cover being slidably connected to the distal end of the elongate body, the cover being movable from a stored position, in which the rotatable cutting element is covered by the cover, to a working position, in which at least part of the rotatable cutting element is exposed outside the cover, the proximal end of the cover being axially aligned with the distal end of the elongate body when the cover is in the stored position, the proximal end of the cover being axially offset in a radial direction from the distal end of the elongate body when the cover is in the working position, the longitudinal axis of the cover being axially aligned with the longitudinal axis of the elongate body when the cover is in the stored position, the longitudinal axis of the cover being axially offset in a radial direction from the longitudinal axis of the elongate body when the cover is in the working position.

2. The device of claim 1, wherein:
the cover further includes a tissue collection chamber, and wherein the cover is configured such that during use tissue cut by the cutting element is directed into the collection chamber.

3. The device of claim 1, wherein:
the cover forms a distal tip.

4. The device of claim 1, wherein:
the longitudinal axis of the cover is substantially parallel to the longitudinal axis of the elongate body when the cover is in the working position.

5. The device of claim 1, wherein:
the cover is configured to be slidable relative to the elongate body to a plurality of different working positions, an amount of the rotatable cutting element exposed being different in each working position.

6. The device of claim 1, wherein:
the cover is configured to translate when moving to the working position without substantial deformation of the cover.

7. The device of claim 1, further comprising:
a visualization element positioned at a radially outer position relative to the elongate body.

8. The device of claim 7, wherein:
the visualization element is movable relative to the elongate body.

9. The device of claim 1, wherein:
the cover is naturally biased to the stored position.

10. The device of claim 1, wherein:
the cover is linearly slidable relative to the elongate body at an angle which is not parallel to a longitudinal axis of the elongate body.

11. The device of claim 1, wherein:
the cover is connected to the body by a slot and pin engagement so that the cover translates linearly relative to the body when moved from its stored position to its working position.

* * * * *